(12) United States Patent
Hartmann

(10) Patent No.: US 9,737,235 B2
(45) Date of Patent: Aug. 22, 2017

(54) SYSTEM AND METHOD FOR IMAGE-GUIDED NAVIGATION

(75) Inventor: Steven L. Hartmann, Superior, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 1369 days.

(21) Appl. No.: 12/400,273

(22) Filed: Mar. 9, 2009

(65) Prior Publication Data
US 2010/0228117 A1 Sep. 9, 2010

(51) Int. Cl.
| | | |
|---|---|---|
| *A61B 5/05* | (2006.01) | |
| *A61B 5/06* | (2006.01) | |
| *A61B 5/11* | (2006.01) | |
| *A61B 6/00* | (2006.01) | |
| A61B 5/00 | (2006.01) | |
| A61B 6/04 | (2006.01) | |
| A61B 34/20 | (2016.01) | |
| A61B 90/00 | (2016.01) | |

(52) U.S. Cl.
CPC ............ *A61B 5/06* (2013.01); *A61B 5/064* (2013.01); *A61B 5/1127* (2013.01); *A61B 6/4233* (2013.01); *A61B 6/4405* (2013.01); *A61B 6/4441* (2013.01); *A61B 6/466* (2013.01); *A61B 6/547* (2013.01); *A61B 34/20* (2016.02); *A61B 5/062* (2013.01); *A61B 5/4504* (2013.01); *A61B 6/0421* (2013.01); *A61B 2034/2051* (2016.02); *A61B 2034/2055* (2016.02); *A61B 2090/3762* (2016.02)

(58) Field of Classification Search
USPC ................................ 600/407, 424, 426, 429
See application file for complete search history.

(56) References Cited

U.S. PATENT DOCUMENTS

| | | | |
|---|---|---|---|
| 5,592,939 A | 1/1997 | Martinelli | |
| 5,913,820 A | 6/1999 | Bladen et al. | |
| 6,235,038 B1 * | 5/2001 | Hunter ................ | A61B 90/36 600/417 |
| 6,402,762 B2 | 6/2002 | Hunter et al. | |
| 6,474,341 B1 | 11/2002 | Hunter et al. | |
| 6,747,539 B1 | 6/2004 | Martinelli | |
| 6,856,828 B2 * | 2/2005 | Cossette et al. ............. | 600/429 |
| 6,940,941 B2 | 9/2005 | Gregerson et al. | |

(Continued)

FOREIGN PATENT DOCUMENTS

| | | |
|---|---|---|
| FR | 2908628 A1 | 5/2008 |
| WO | WO-9927839 A2 | 6/1999 |
| WO | WO-2007014470 A2 | 2/2007 |

OTHER PUBLICATIONS

"AxiEM Electromagetic Navigation," tri-fold brochure, Medtronic Navigation (2005) 2 pages.
"Medtronic Computer-Assisted Surgery," brochure, Medtronic Navigation, Inc. (2005) pp. 1-29.

(Continued)

*Primary Examiner* — Unsu Jang
*Assistant Examiner* — Shahdeep Mohammed
(74) *Attorney, Agent, or Firm* — Harness Dickey

(57) ABSTRACT

Image data can be obtained with an imaging device. A location of the imaging device relative to a subject can be determined. A location of an instrument can be tracked relative to the subject using two or more tracking systems operating with different tracking modalities. Also, the tracked location of the instrument can be illustrated relative to the image data.

36 Claims, 10 Drawing Sheets

(56) References Cited

U.S. PATENT DOCUMENTS

| | | | |
|---|---|---|---|
| 7,001,045 B2 | 2/2006 | Gregerson et al. | |
| 7,106,825 B2 | 9/2006 | Gregerson et al. | |
| 7,107,091 B2 * | 9/2006 | Jutras et al. | 600/429 |
| 7,108,421 B2 | 9/2006 | Gregerson et al. | |
| 7,188,998 B2 | 3/2007 | Gregerson et al. | |
| RE40,852 E | 7/2009 | Martinelli et al. | |
| RE41,066 E | 12/2009 | Martinelli et al. | |
| 7,751,865 B2 | 7/2010 | Jascob et al. | |
| 2001/0011175 A1 * | 8/2001 | Hunter et al. | 606/130 |
| 2001/0036245 A1 * | 11/2001 | Kienzle et al. | 378/4 |
| 2003/0117135 A1 | 6/2003 | Martinelli et al. | |
| 2004/0013225 A1 * | 1/2004 | Gregerson et al. | 378/19 |
| 2004/0019263 A1 | 1/2004 | Jutras et al. | |
| 2004/0116803 A1 | 6/2004 | Jascob et al. | |
| 2004/0127788 A1 | 7/2004 | Arata | |
| 2004/0199072 A1 | 10/2004 | Sprouse et al. | |
| 2005/0165292 A1 * | 7/2005 | Simon et al. | 600/407 |
| 2005/0245817 A1 * | 11/2005 | Clayton et al. | 600/424 |
| 2006/0025677 A1 | 2/2006 | Verard et al. | |
| 2006/0084867 A1 | 4/2006 | Tremblay et al. | |
| 2007/0066887 A1 * | 3/2007 | Mire et al. | 600/424 |
| 2008/0171937 A1 | 7/2008 | Dukesherer et al. | |
| 2008/0172069 A1 | 7/2008 | Dukesherer et al. | |
| 2008/0275334 A1 * | 11/2008 | Berting | 600/424 |
| 2008/0300478 A1 | 12/2008 | Zuhars et al. | |
| 2009/0240141 A1 * | 9/2009 | Neubauer et al. | 600/426 |
| 2009/0287443 A1 | 11/2009 | Jascob et al. | |
| 2010/0210939 A1 | 8/2010 | Hartmann et al. | |

OTHER PUBLICATIONS

"StealthStation® Tria™ plus Treatment Guidance System," brochure, Medtronic Surgical Navigation Technologies (2004) 2 pages.

"Treon, StealthStation," brochure, Medtronic Surgical Navigation Technologies (2001) 8 pages.

Foley, "The StealthStation: Three-Dimensional Image-Interactive Guidance for the Spine Surgeon," Spinal Frontiers, Apr. 1996, pp. 7-9.

International Search Report and Written Opinion mailed Jun. 30, 2010 for PCT/US2010/023612 filed Mar. 5, 2010, claiming benefit of U.S. Appl. No. 12/400,273, filed Mar. 9, 2009.

International Preliminary Report on Patentability and Written Opinion mailed Sep. 20, 2011 for PCT/US2010/023612 filed Mar. 5, 2010, claiming benefit of U.S. Appl. No. 12/400,273, filed Mar. 9, 2009.

International Search Report and Written Opinion mailed Apr. 14, 2011 for PCT/US2010/026312 filed Mar. 5, 2010, claiming benefit of U.S. Appl. No. 12/400,273, filed Mar. 9, 2009.

Communication pursuant to Article 94(3) EPC dated Jul. 29, 2015 for European Application No. 107266793-1654.

Communication pursuant to Article 94(3) EPC dated Apr. 7, 2016 for Application No. 10726679.3.

Communication pursuant to Article 94(3) EPC for European Application No. 107266793 mailed Jan. 11, 2017 corresponding to PCT/US2010/026312 claiming brenefit of U.S. Appl. No. 12/400,273, filed Mar. 9, 2009.

European Office Action dated Jun. 7, 2017 in corresponding European Application No. 10726679.3.

* cited by examiner

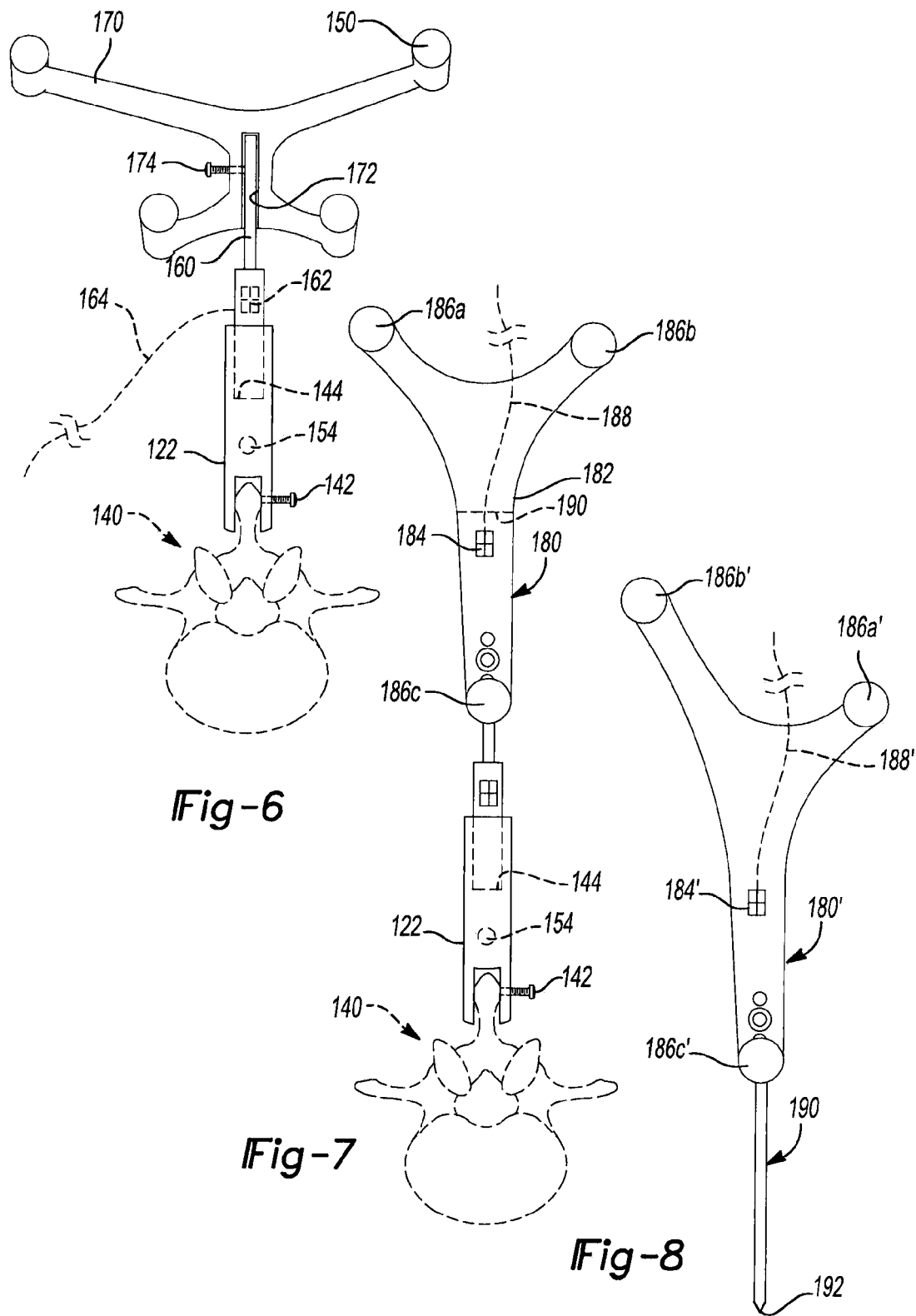

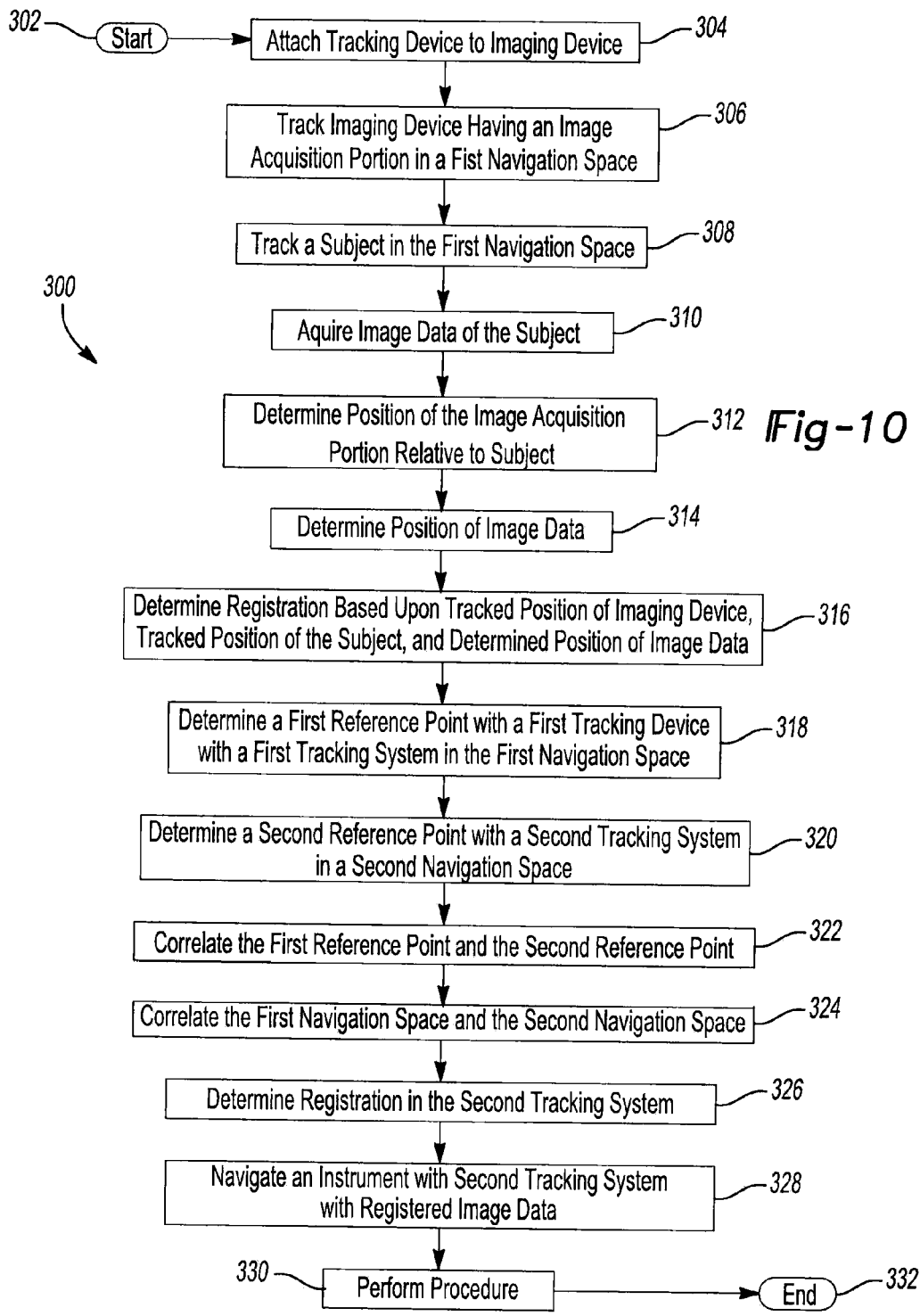

SYSTEM AND METHOD FOR IMAGE-GUIDED NAVIGATION

FIELD

The present disclosure relates generally to navigated surgery, and more specifically, to a method and apparatus for performing a surgical procedure with the use of more than one surgical navigation modality.

BACKGROUND

Image guided procedures, such as surgical procedures, can utilize image data obtained prior to or during a medical procedure to assist a user, such as a surgeon, in performing and navigating a procedure. Such procedures can be referred to as navigated, guided, or computer assisted surgery procedures. Recent advances in imaging technology, especially in imaging technologies that produce high-detailed, two, three, and four dimensional image data (e.g. computed tomography (CT), magnetic resonance imaging (MRI), fluoroscopic imaging (such as with a C-arm device), positron emission tomography (PET), and ultrasound (US) imaging) has increased the interest in navigated surgical procedures.

In one example, navigation systems may require a dynamic reference frame to track the position of the patient should patient movement occur during the navigated procedure. The dynamic reference frame can be affixed to the patient. The dynamic reference frame can move with the patient to maintain a registration between image space and patient space.

SUMMARY

An instrument can be tracked during an operative procedure. The instrument can be illustrated as an icon or representation superimposed on acquired image data to identify the position of the instrument relative to patient space. To allow for navigation, the instrument may include a tracking device. The tracking device can include a trackable portion, such as an electromagnetic coil or an optical detection member, which may be detected by a suitable tracking system. The tracking device may consist entirely of the trackable portion or may include a mount or fixture for the trackable portion. The tracking device can also include more than one tracking device all associated with each other and connected to a separate member. Also, a dynamic reference frame (DRF) can be used by the tracking system to maintain a registration or localization of the patient space to the image space. The DRF can also include any appropriate tracking device that is fixed to a portion of the patient that allows the tracking system to determine whether the patient has moved and to where. Tracking patient movement can allow registration to image space to be maintained.

The tracking system can also track the imaging device that acquires the image data. In so doing, registration of the image space to patient space can occur without user intervention. The tracking system can determine both the position of the patient and the position of the imaging device during image data acquisition.

BRIEF DESCRIPTION OF THE DRAWINGS

The present teachings will become more fully understood from the detailed description and the accompanying drawings, wherein:

FIGS. 5-9 are diagrammatic environmental views of two tracking devices operable in two tracking modalities to track a subject according to various embodiments that may be distinct or combinable; and FIG. 10 is a flowchart illustrating a method of performing a navigated procedure with more than one tracking system.

DETAILED DESCRIPTION OF VARIOUS EMBODIMENTS

The following description of various embodiments is merely exemplary in nature and is in no way intended to limit the teachings, its application, or uses. By way of example, the following description is directed toward a spinal surgical procedure. It is appreciated, however, that the following may be used for other image guided surgeries such as other orthopedic procedures, cardiac procedures, neurological procedures, or any other surgical or medical procedure.

Figure 1:
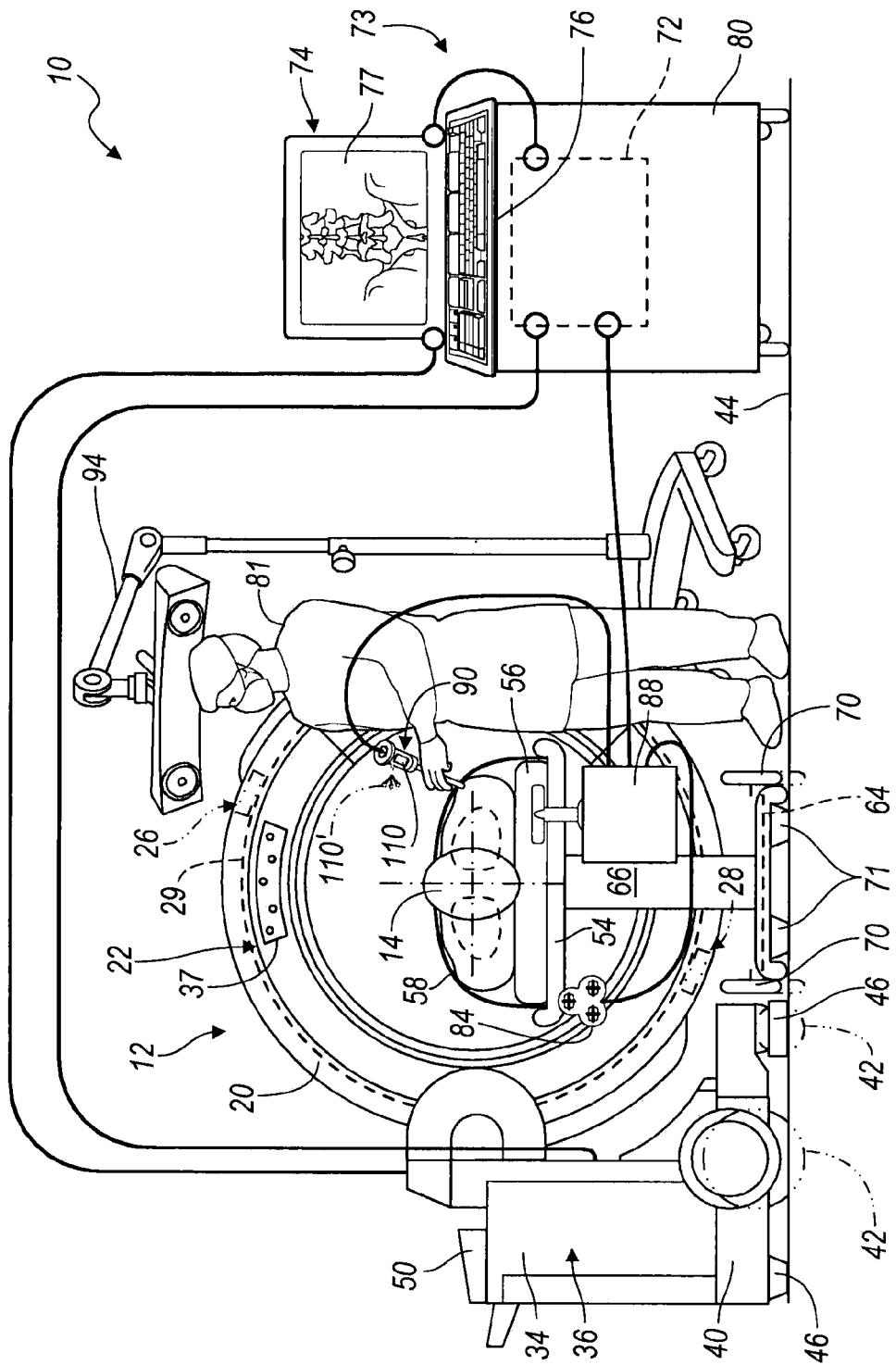
FIG. 1 is a diagram of a navigation system according to various embodiments including an imaging device and tracking system.

FIG. 1 is a diagram illustrating an overview of a navigation system 10 that can be used for various procedures. The navigation system 10 can be used to track the location of an implant, such as a spinal implant or orthopedic implant, relative to a patient 14. Also, the navigation system 10 can track the position and orientation of an instrument 90, such as a biopsy needle or resection instrument. It should further be noted that the navigation system 10 may be used to navigate any type of instrument, implant, or delivery system, including: guide wires, arthroscopic systems, orthopedic implants, spinal implants, deep brain stimulation (DBS) probes, etc. Moreover, the instruments may be used to navigate or map any region of the body. The navigation system 10 and the various instruments may be used in any appropriate procedure, such as one that is generally minimally invasive or an open procedure.

The navigation system 10 includes an imaging device 12 that is used to acquire pre-, intra-, or post-operative or real-time image data of a subject, such as a patient 14. It will be understood, however, that any appropriate subject can be imaged and any appropriate procedure may be performed relative to the subject. In the example shown, the imaging device 12 comprises an O-arm® imaging device sold by Medtronic Navigation, Inc. having a place of business in Louisville, Colo., USA. The imaging device 12 may have a generally annular gantry housing 20 and an image capturing portion 22. The image capturing portion 22 may include an x-ray source or emission portion 26 and an x-ray receiving or image receiving portion 28 located generally or as practically possible 180 degrees from each other and mounted on a rotor (not illustrated) relative to a track or rail 29. The image capturing portion 22 can be operable to rotate 360 degrees during image acquisition. The image capturing portion 22 may rotate around a central point or axis, allowing image data of the patient 14 to be acquired from multiple directions or in multiple planes. The imaging device 12 can include those disclosed in U.S. Pat. Nos. 7,188,998; 7,108,421; 7,106,825; 7,001,045; and 6,940,941; all of which are incorporated herein by reference. In one example, the imaging device 12 can utilize flat plate technology having a 1,720 by 1,024 pixel viewing area.

The position of the image capturing portion 22 can be precisely known relative to any other portion of the imaging device 12. In addition, as discussed herein, the precise knowledge of the position of the image capturing portion 22 can be used in conjunction with a tracking system to determine the position of the image capturing portion 22 and the image data relative to the tracked subject, such as the patient 14.

The imaging device 12 can be tracked with a tracking device 37. The tracking device 37 can include or consist only of a trackable portion. Due to inclusion of the tracking device 37 on the imaging device 12 within the navigation system 10 and/or the determinable precise location of the image capturing portion 22 that acquires the image data of the patient 14, the image data defining an image space acquired of the patient 14 can be inherently or automatically registered relative to a patient space of the patient 14 in the navigation system 10. It will be understood, however, that image data can be acquired of any subject (e.g. a patient, a workpiece, etc.) which would define subject space. Registration allows for a translation between patient space and image space.

The tracking device 37 can include an optical tracking device. The optical tracking device can emit or reflect optical energy, such as infrared, ultraviolet, visible, etc. The optical energy can be received by an optical localizer 94, discussed herein, and the position of the tracking device 37 and the imaging device 12 can be determined with the navigation system 10. An optical tracking system, associated with the tracking device 37 and the optical localizer 94, can be generally unaffected or no disturbance is introduced into the tracking system due to large metal objects. Other tracking systems, however, such as an EM tracking system, can be used to track the imaging device 12. Even if the imaging device 12 may interfere or distort EM fields used with the EM tracking system, the distortions can be accounted for or shielded with the EM tracking system. Exemplary shielding systems include those in U.S. patent application Ser. No. 10/252,258, filed on Sep. 23, 2002, published as U.S. Pat. App. Pub. No. 2003/0117135 and U.S. Pat. No. 6,747,539, issued on Jun. 8, 2004; distortion compensation systems can include those disclosed in U.S. patent application Ser. No. 10/649,214, filed on Jan. 9, 2004, published as U.S. Pat. App. Pub. No. 2004/0116803, all of which are incorporated herein by reference.

The patient 14 can also be tracked or fixed within the navigation system 10 to allow for registration. As discussed further herein, registration of the image space to the patient space or subject space allows for navigation of the instrument 90 with the image data. When navigating the instrument 90, a position of the instrument 90 can be illustrated relative to image data acquired of the patient 14 on a display device 74. Various tracking systems, such as one including an electromagnetic (EM) localizer 84 or an optical localizer 94 can be used to track the instrument 90.

More than one tracking system can be used to track the instrument 90 in the navigation system 10. According to various embodiments, this can occur if both of the tracking systems, e.g., the EM localizer 84 and the optical localizer 94, include an identical frame of reference or are correlated. The frame of reference can include a reference frame, such as a dynamic reference frame, connected to the patient 14. It will be understood, however, that the reference frame can be attached to any appropriate portion, such as the imaging device 12. The reference frame can be maintained or used to correlate the two tracking systems at a selected point, such as with one or more reference points. The use of one or more tracking systems, and specifically the use of two tracking systems within the single navigation system 10, is discussed in further detail herein.

Figure 1A:
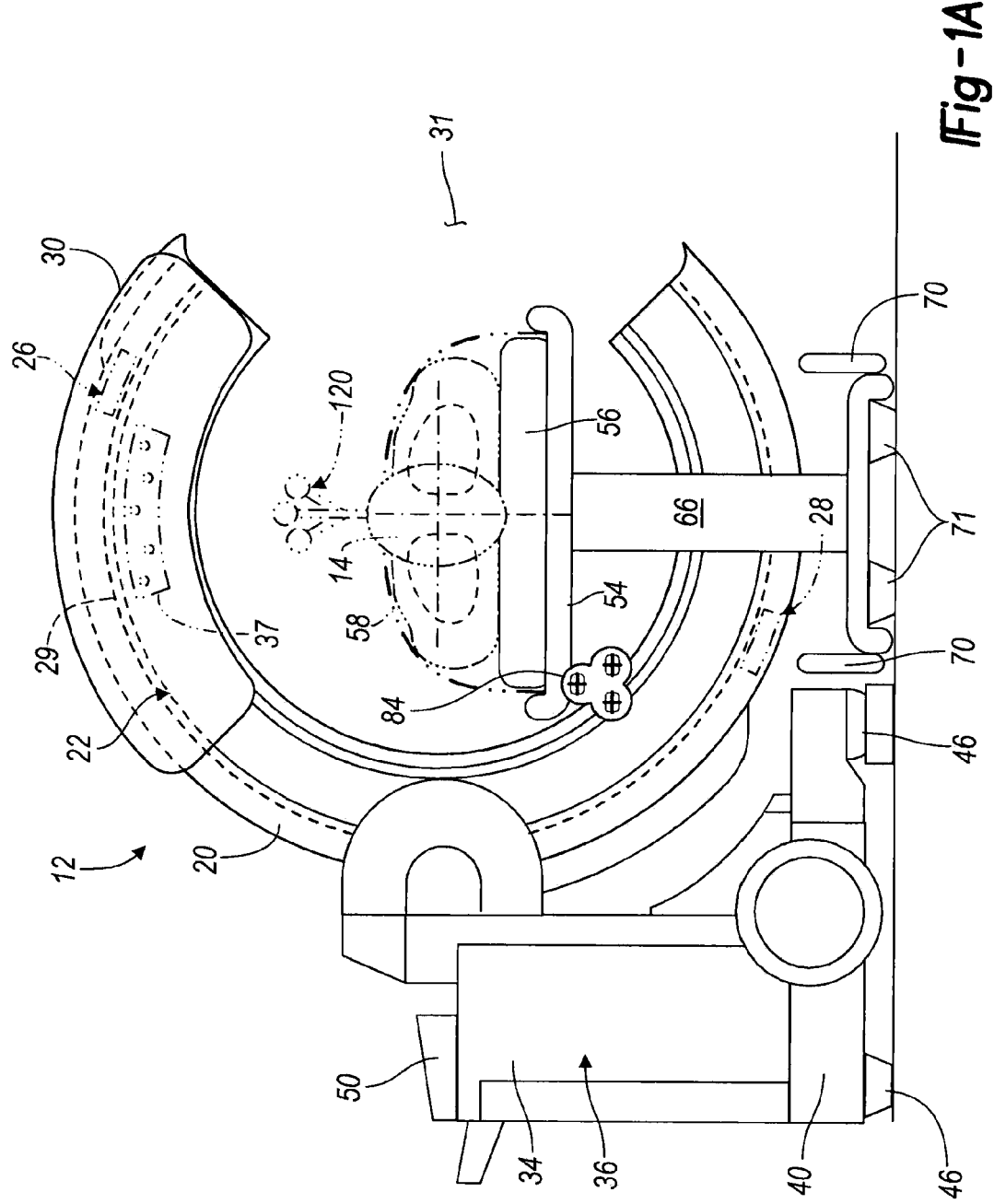
FIG. 1A diagrammatically illustrates the imaging system operable to open and move a subject within an annular opening.
Figure 2:
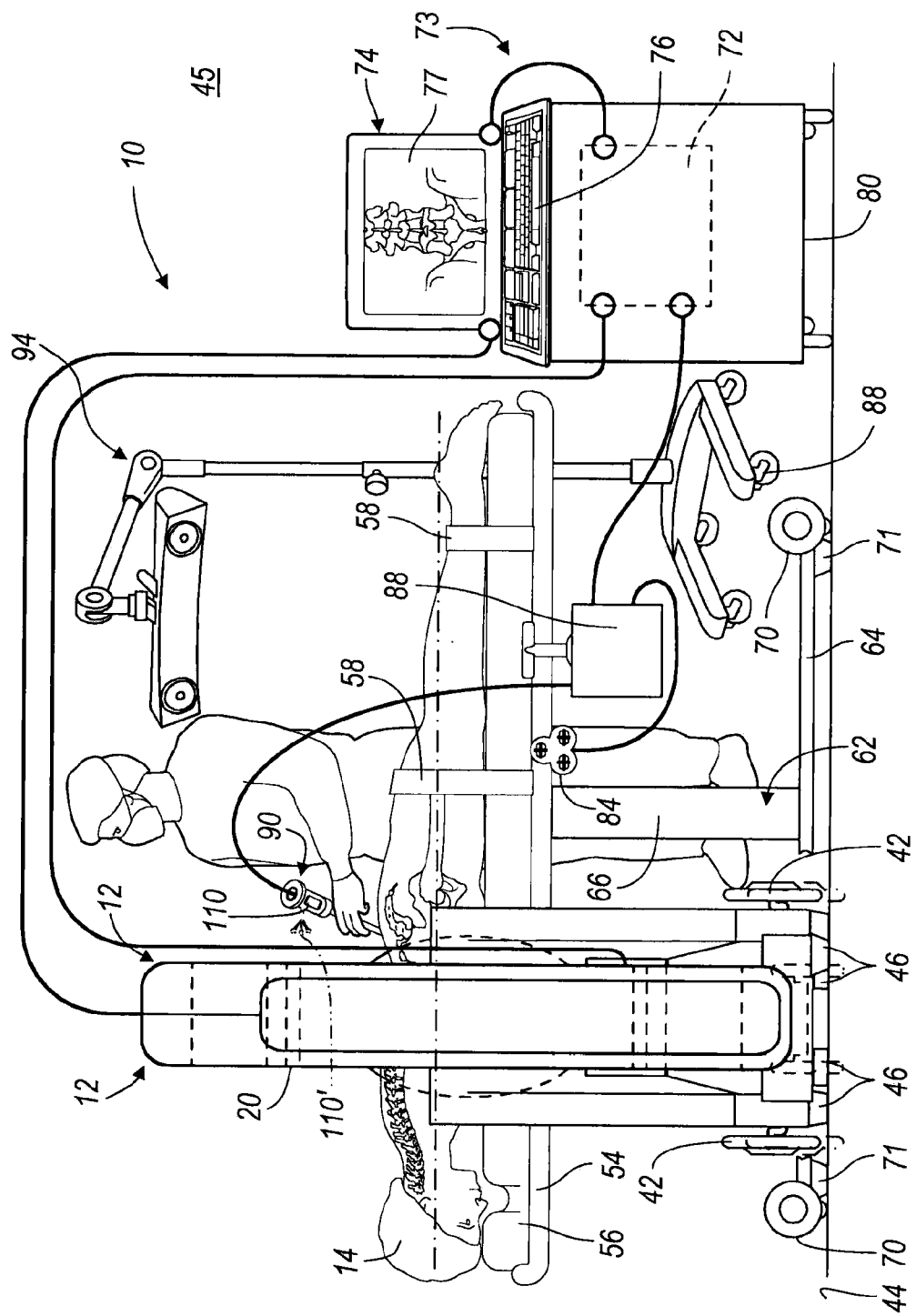
FIG. 2 is a lateral view of the subject positioned relative to the navigation system of FIG. 1.
Figure 3:
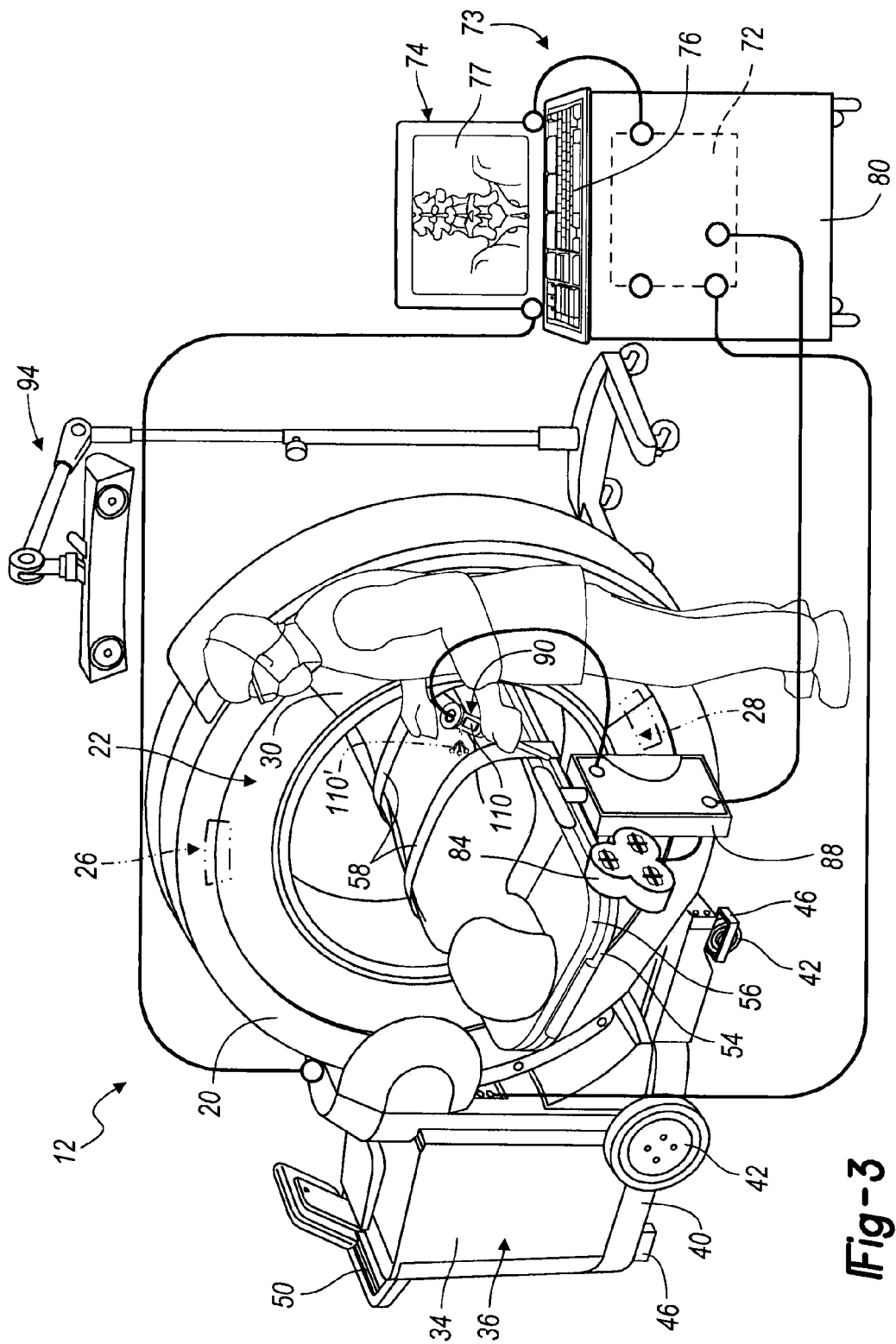
FIG. 3 is a perspective view of the navigation system of FIG. 1.

The imaging device 12 can further include a door section 30 in the housing 20. The door section 30 can be movable to create a lateral access or passage 31 for receiving the patient 14, as illustrated in FIG. 1A. The circular housing 20 can be generally fixedly connected to a support housing or cart 34 associated with or including a processing unit 36. The imaging device 12 provides an accurate and robust imaging device to capture image data of the patient 14. In this regard, unlike C-arms that can flex, the imaging device 12 includes the housing 20, rail 29, and other portions that remain substantially static, at least relative to one another.

The cart 34 can include a base 40 having a plurality of wheels 42. The wheels 42 can be movable between a transporting position (phantom) and an operating position (solid). Thus, the imaging device 12 provides a substantially large or stable base substantially ensures a fixed position over time, even with slight vibrations. The structure of the imaging device 12 as a whole and specifically the relationship between the circular housing 20 and the cart 34 can provide a rigid and stable structure in the operating position. In this way, there exists substantially no flexing, bowing or other dynamic movement of the imaging device 12 relative to the patient 14 in the operating position as may exist with other imaging devices. As a result, the imaging device 12 or portions thereof may not move subsequent to image acquisition or once the location of the patient 14 is determined that may alter the determined location of the acquired image data.

It is appreciated, however, that an imaging device other than a fluoroscopic C-arm may be used. The imaging device 12 can be any appropriate imaging device and can include a system to determine its position relative to a subject, such as the patient. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc.

An imaging device controller 50 that may control the imaging device 12 can receive the image data generated at the image capturing portion 22 and store the images for later use. The controller 50 can also control the rotation of the image capturing portion 22 of the imaging device 12. The controller 50 can also instruct the door 30 to move during initial positioning relative to the patient 14. It will be understood that the controller 50 need not be integral with the processing unit or processing portion 36 and may include a second and separate processor, such as that in a portable computer.

The patient 14 can be fixed onto an operating table 54. According to one example, the table 54 can be a Axis Jackson® operating table sold by OSI, a subsidiary of Mizuho Ikakogyo Co., Ltd., having a place of business in Tokyo, Japan or Mizuho Orthopedic Systems, Inc having a place of business in California, USA. The table 54 can include a generally horizontal patient accepting portion 56 and a plurality of straps 58. The straps 58 can be secured around the patient 14 to fix the patient 14 relative to the table 54. Various apparatuses may be used to position the patient 14 in a static position on the operating table 54. Examples of such patient positioning devices are set forth in commonly assigned U.S. patent application Ser. No. 10/405,068 entitled "An Integrated Electromagnetic Navigation And Patient Positioning Device", filed Apr. 1, 2003 which is hereby incorporated by reference. Other known apparatuses may include a Mayfield® clamp.

The table 54 can include a stand 62 having a lower platform 64 and a vertical support 66. The vertical support 66 can be disposed between the patient accepting portion 56 and the lower platform 64. The lower platform 64 can include a plurality of wheels 70. The wheels 70 can be movable between a transporting position phantom and an operating position solid.

The lower platform 64 may also include a plurality of feet 71. The feet 71 may be formed of resilient material suitable to securely engage and resist movement relative to the floor 44 when the wheels 70 are in the operating position. As can be appreciated, once the table 54 has been suitably placed in the operating room 45, the wheels 70 can be moved to the operating position. In the operating position, the feet 71 can engage the floor 44 and render the table 54 static with respect to the floor 44. It is appreciated that the feet 71 can be configured differently or be eliminated entirely. Further, other arrangements may be provided for locating the table 54 in a static position. Because the straps 58 can secure the patient 14 in a static position relative to the patient receiving portion 56, and the table 54 can be fixed relative to the floor 44, the patient 14 can be fixed relative to the floor 44. The table 54 can be integral with the imaging device 12 and hence at a known location relative to the imaging device 12 or fixed at a known location relative to the imaging device 12.

Also, the position of the patient 14 relative to the imaging device can be determined by the navigation system 10. The tracking device 37 can be used to track and locate at least a portion of the imaging device 12, for example the housing 20. The patient 14 can be tracked with a tracking device, such as one used as a dynamic reference frame, as discussed further herein. Accordingly, the position of the patient 14 relative to the imaging device 12 can be determined. Further, the location of the imaging portion 22 can be determined relative to the housing 20 due to its precise position on the rail 29 within the housing 20, substantially inflexible rotor, etc. The imaging device 12 can include an accuracy of within about 10 microns, for example, if the imaging device 12 is an O-Arm® imaging device sold by Medtronic Navigation, Inc. having a place of business in Louisville, Colo. The O-arm® or appropriate imaging device can know its position and be repositioned to the same position within about 10 microns. This allows for a substantially precise placement of the imaging device and precise determination of the position of the imaging device 12. Precise positioning of the imaging portion 22 is further described in U.S. Pat. Nos. 7,188,998; 7,108,421; 7,106,825; 7,001,045; and 6,940,941; all of which are incorporated herein by reference, In operation, the imaging device 12 generates and/or emits x-rays from the x-ray source 26 that propagate through the patient 14 and are received by the x-ray imaging receiving portion 28. The image capturing portion 22 generates image data representing the intensities of the received x-rays. Typically, the image capturing portion 22 can include an image intensifier that first converts the x-rays to visible light and a camera (e.g. a charge couple device) that converts the visible light into digital image data. The image capturing portion 22 may also be a digital device that converts x-rays directly to digital image data for forming images, thus potentially avoiding distortion introduced by first converting to visible light.

Two dimensional and/or three dimensional fluoroscopic image data that may be taken by the imaging device 12 can be captured and stored in the imaging device controller 50. Multiple image data taken by the imaging device 12 may also be captured and assembled to provide a larger view or image of a whole region of a patient 14, as opposed to being directed to only a portion of a region of the patient 14. For example, multiple image data of the patient's 14 spine may be appended together to provide a full view or complete set of image data of the spine.

The image data can then be forwarded from the image device controller 50 to a navigation computer and/or processor 72 that can be a part of a controller or work station 73 having the display 74 and a user interface 76. It will also be understood that the image data is not necessarily first retained in the controller 50, but may also be directly transmitted to the work station 73. The work station 73 can provide facilities for displaying the image data as an image 77 on the display 74, saving, digitally manipulating, or printing a hard copy image of the received image data. The user interface 76, which may be a keyboard, mouse, touch pen, touch screen or other suitable device, allows a user 81 to provide inputs to control the imaging device 12, via the image device controller 50, or adjust the display settings of the display 74. The work station 73 may also direct the image device controller 50 to adjust the image capturing portion 22 of the imaging device 12 to obtain various two-dimensional images along different planes in order to generate representative two-dimensional and three-dimensional image data.

When the x-ray source 26 generates the x-rays that propagate to the x-ray image receiving portion 28, radiation sensors (not specifically shown) can sense the presence of radiation, which is forwarded to the image device controller 50, to identify whether or not the imaging device 12 is actively imaging (e.g. acquiring image data). This information can also be transmitted to a coil array controller 80, if an electromagnetic tracking system is employed, as further discussed herein. The navigation processor 72, tracking processor, or any appropriate portion can identify when image data is being acquired to determine a location of the imaging device 12 at the time of imaging. Alternatively, the user 81 may manually indicate when the imaging device 12 is actively imaging or this function can be built into the x-ray source 26, x-ray image receiving portion 28, or the image device controller 50.

With continuing reference to FIG. 1, the navigation system 10 can further include a tracking system such as an electromagnetic (EM) navigation tracking system. The EM tracking system can include the electromagnetic (EM) localizer 84, which can include a transmitter coil array. The EM tracking system can also include an EM controller 88 and the instrument 90. The EM controller 88 can control the EM localizer 84 (such as powering the coils and controlling the coils) and interface with the instrument 90 or other tracked members or tracking devices. The localizer or transmitter coil array 84 can be attached directly to the image device 12, attached to the OR table 54, or any other appropriate location. The instrument 90 may be any appropriate instrument, for example, the instrument 90 may be used for preparing a portion of the patient 14, such as a biopsy needle, or positioning an implant. The EM tracking system may include the STEALTHSTATION® AXIEM™ Navigation System, sold by Medtronic Navigation, Inc. having a place of business in Louisville, Colo.; or it can be any EM tracking system described in U.S. patent application Ser. No. 10/941,782, filed Sep. 15, 2004, and entitled "METHOD AND APPARATUS FOR SURGICAL NAVIGATION", herein incorporated by reference. It will be understood that the tracking system may also be or include any appropriate tracking system, including a STEALTHSTATION® TRIA®, TREON®, and/or S7™ Navigation System having an optical localizer, similar to the optical localizer 94, sold by Medtronic Navigation, Inc. having a place of business in Louisville, Colo. Other tracking systems include an acoustic, radiation, radar, etc. tracking or navigation systems.

It is further noted that the entire tracking system or parts of the tracking system may be incorporated into the imaging device 12, including the work station 73, radiation sensors, localizers, 84, 94, etc. Incorporating the tracking system can provide an integrated imaging and tracking system.

The operation of the EM tracking system is generally known and not repeated here in detail. Briefly, however, the transmitter coil array 84 can include a plurality of coils and each can be generate selected electromagnetic fields in a navigation space of the subject, such as the patient 14. The subject space or patient space is the physical space occupied by or near the subject or patient. The navigation field can at least partially overlap the subject or patient space. Discussion herein of patient space will be understood to be a specific example of subject space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, both of which are hereby incorporated by reference.

The EM controller 88 can drive each coil in the EM localizer 84 in a time division multiplex or a frequency division multiplex manner. In this regard, each coil may be driven separately at a distinct time or all of the coils may be driven simultaneously with each being driven by a different frequency. Upon driving the coils in the EM localizer 84 with the EM controller 88, electromagnetic fields can be generated which define the navigation space.

The electromagnetic fields generated in the patient space can induce currents in an EM tracking device 110 positioned on or in the instrument 90. These induced signals from the EM tracking device 110 can be transmitted to the EM controller 88 and/or the processor 72. The EM controller 88 may provide all the necessary electrical isolation for the navigation system 10. Alternatively, the electrical isolation may also be provided in a separate device. The EM controller 88 can also include amplifiers, filters and buffers to directly interface with the EM tracking device 110. Alternatively, the instrument 90 may employ a wireless communications channel, such as that disclosed in U.S. Pat. No. 6,474,341, entitled "Surgical Communication Power System," issued Nov. 5, 2002, herein incorporated by reference, as opposed to being coupled directly to EM controller 88. Also, the tracking device 110 can generate a field sensed by the EM localizer 84 to track the tracking device 110.

The EM tracking device 110 can consist entirely of a trackable portion, such as one or more coils. The tracking device 110, however, may also include a mount or structure for holding the trackable portion in a selected location. For example, the tracking device 110 can include a coil (i.e. the trackable portion) and a mount to fix the trackable portion to the instrument 90. Likewise, a tracking device according to various embodiments can consist only of a trackable portion, such as a coil, a reflective member, or a light emitting member, and a mount to hold the trackable portion in a selected location.

Various portions of the navigation system 10, such as the instrument 90, and others as will be described in detail below, can be equipped with at least one, and generally multiple, of the tracking devices 110. The instrument can also include more than one type or modality of tracking device, such as the EM tracking device 110 and an optical tracking device 110'. The instrument 90 can be a biopsy needle, handle or inserter that interconnects with an attachment and may assist in placing an implant. The instrument 90 can include a graspable or manipulable portion at a proximal end and the tracking devices 110, 110' may be fixed near the manipulable portion of the instrument 90.

The EM tracking device 110 can be replaced by or used in conjunction with any appropriate tracking device, such as an optical tracking device 110', acoustic device, or a radar device. The optical tracking system can include that discussed above, such as the STEALTHSTATION® TREON® Tracking System sold by Medtronic Navigation, Inc. Generally, the optical localizer 94 can include one or more cameras operable to receive an optical signal from the optical tracking device 110'. The optical signal can be one actively emitted by the optical tracking device 110', such as with an L.E.D. emitter, or one reflected from reflector portions of the optical tracking device 110'. If the optical signals are a reflected signal, the emitted energy can be from a light, such as a visible or infrared light, associated or connected to the optical localizer 94. The field of view of the optical localizer can define the navigation space of the optical localizer 94.

Additional representative or alternative localization and tracking system is set forth in U.S. Pat. No. 5,983,126, entitled "Catheter Location System and Method," issued Nov. 9, 1999, which is hereby incorporated by reference. The navigation 10 system may be a hybrid system that includes components from various tracking systems.

As discussed above, the patient space and the image space can be registered by identifying matching points or fiducial points in the patient space and respective points in the image space. If both of the tracking systems are registered to the image data or at least correlated to one another, either of the two tracking systems can be used to navigate a procedure. The imaging device 12, such as the O-arm® imaging device sold by Medtronic, Inc. can be used to generate image data at a precise and known position. This can allow image data that is automatically or inherently registered to the patient 14 upon acquisition of the image data.

If during a portion of the procedure, the instrument 90 is selected to be tracked with an EM tracking device 110, the EM localizer 84 can be used to track the position of the instrument 90 including the EM tracking device 110. The EM tracking device 110 can also be used as a DRF. The two tracking systems, using either the EM localizer 84 and/or the optical localizer 94, can be correlated based upon the determination or knowledge of one or more reference points in the navigation spaces of both of the tracking systems. Thus, even if only one tracking system is used to track the imaging device 12 to allow for inherent registration with that tracking system, a correlation to a second tracking system can allow the second tracking system to navigate an instrument with the image data.

Figure 4A:
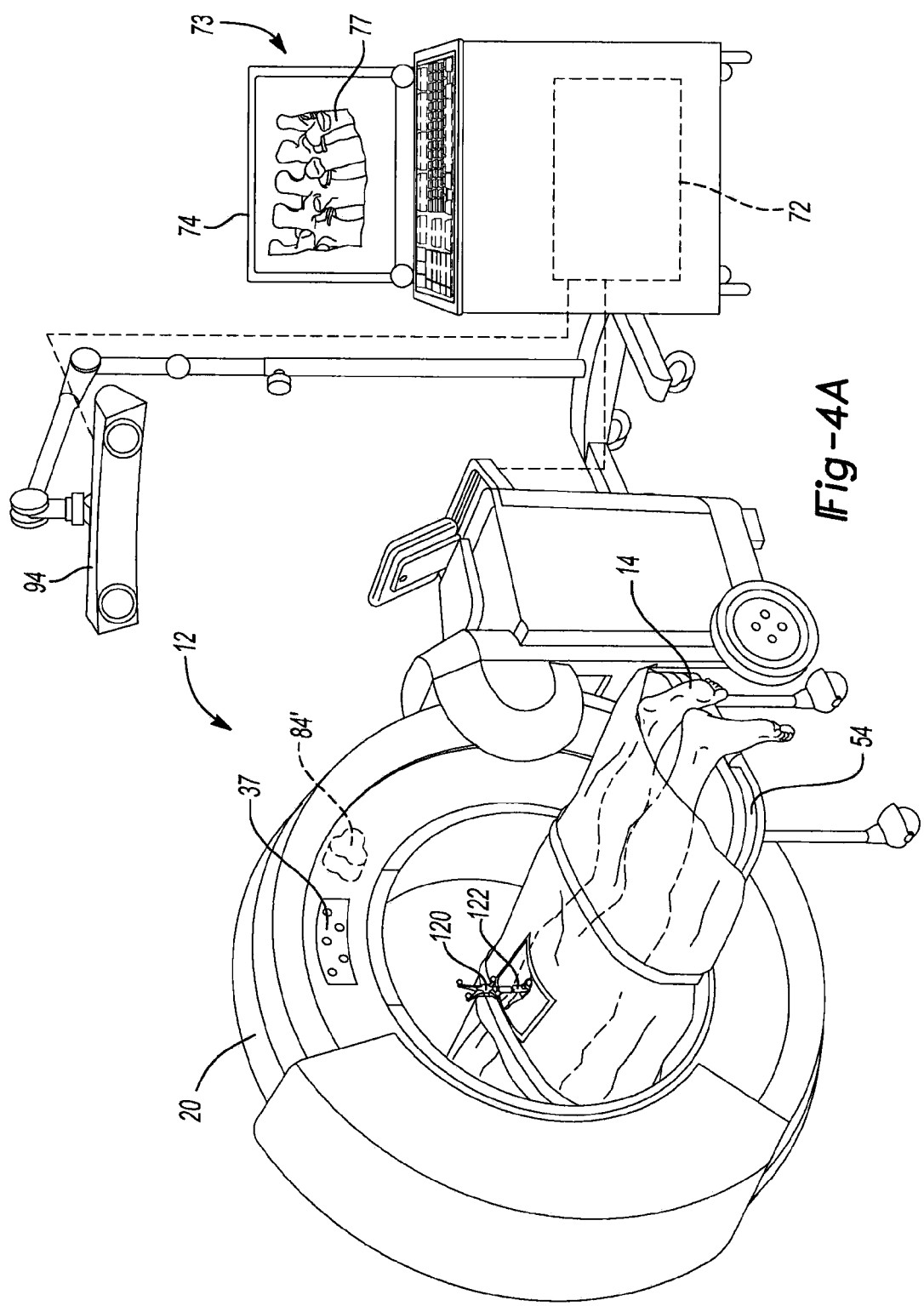
FIG. 4A is a diagrammatic view of a first tracking system operable to track a subject and an imaging device.
Figure 4B:
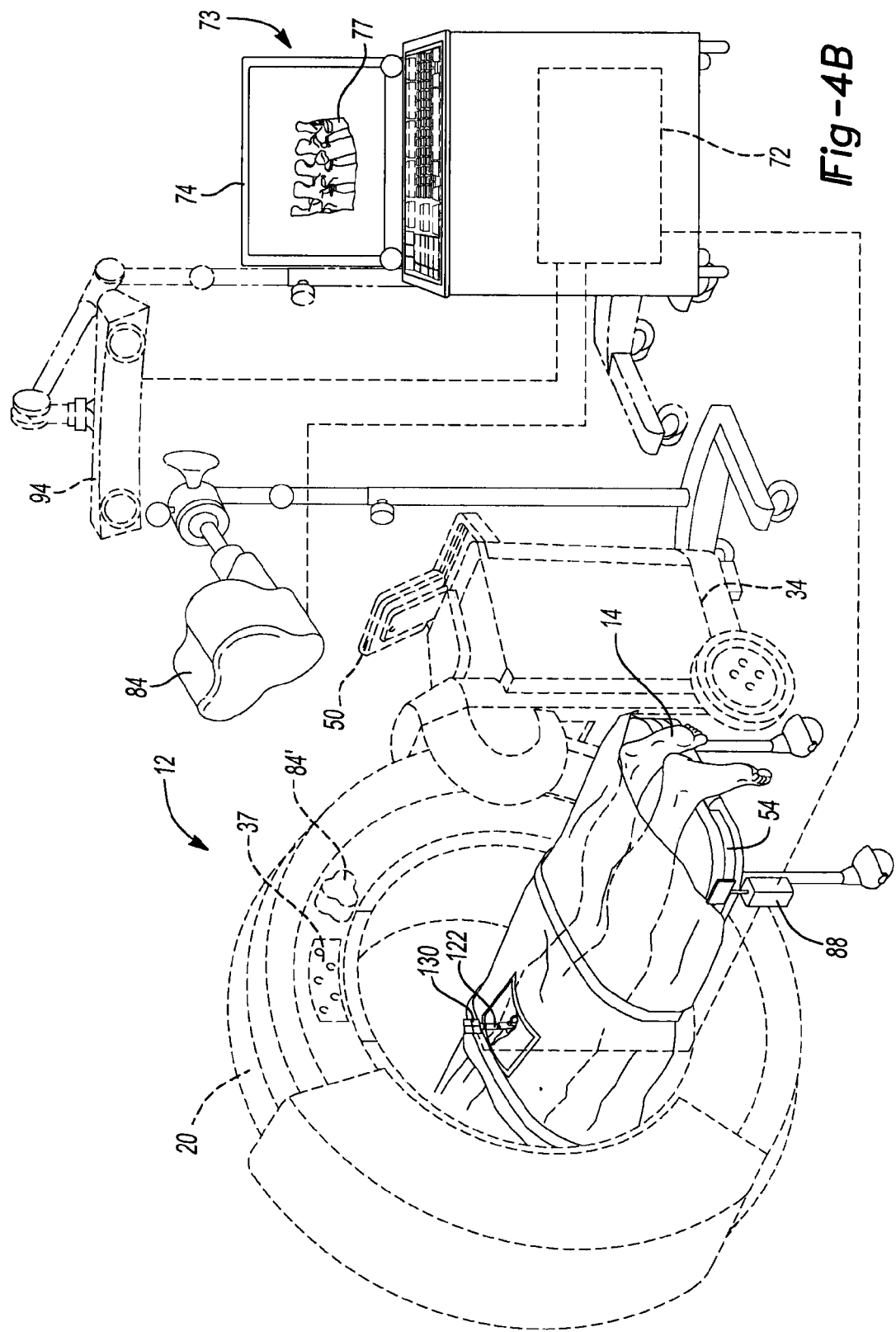
FIG. 4B is a diagrammatic view of a second tracking system operable to track the subject with or without the first tracking system of FIG. 4A.

According to various embodiments, with reference to FIGS. 4A and 4B, the navigation system 10 can include the optical localizer 94 which can be used to track a location of the tracking device 37 associated with the imaging device 12 and an optical tracking device 120 usable as a dynamic reference frame (DRF). The optical tracking device 120 can be interconnected with a base 122 that is further connected to the patient 14. It will be understood that the optical tracking device 120 can be used as any appropriate portion and a DRF is discussed simply as an example of an appropriate optical tracking device portion.

In any case, the optical tracking device 120 can be tracked with the optical localizer 94. The optical localizer 94 is associated with the navigation processor 72 that is operable to determine the position of the optical tracking device 120. In addition, the optical localizer 94 is operable to determine a position of the optical tracking device 37 associated with the imaging device 12. Also, because the patient 14 can be positioned relative to the imaging device in a selected manner, the image acquisition portion 22 allows the position of the image data acquired of the patient 14 to be known substantially precisely relative to a point on the housing 20, patient 14, cart 34, or other physical portion of the imaging device 12.

The tracking device 37 associated with the imaging device 12 enables the navigation processor 72 to substantially know the position of the imaging device 12 in the navigation space. Also, the precise knowledge or determination of an imaging portion of the imaging device can be used by the navigation processor 72 to know the position of the imaging device 12 during image acquisition. The navigation space is that space in which a localizer, such as the optical localizer 94, the electromagnetic localizer 84, or any appropriate tracking localizer, can be used to track a tracking device. It will be understood, that each localizer has a navigation space that can overlap, completely or partially, or be completely separate. As discussed herein, however, the navigation spaces can be correlated. When correlated, all points in each navigation space can be determined relative to one another.

Because the optical localizer 94 is able to track the tracking device 37 a position of where the image data acquired with the imaging device 12 can be substantially precisely determined in the navigation space. The determination of the position of the image data in the navigation space can be used for registration of the patient space to the image space. In other words, because the patient space and the imaging device 12 can both be moved in the navigation space the two can be automatically registered.

Knowing or determining the position of the imaging device 12 in the navigation space when the image data is acquired allows for substantially automatic or inherent registration of the patient space and the image space, because the patient 14 can be tracked with the tracking device 120 in the same navigation space as the imaging device 12. As is generally understood, registration of image space to patient space allows for the generation of a translation map between the patient space and the image space. According to various embodiments, registration can occur by determining points that are substantially identical in the image space and the patient space. The identical points can include anatomical fiducial points or implanted fiducial points.

Because the position of the imaging device 12 is known due to tracking of the imaging device via the tracking device 37, the registration of the image space to the patient space is substantially automatic or inherent once the tracking device 120 is associated with the patient 14 and positioned within the navigation space. The tracking device 120 associated with the patient 14 can be used to identify points in patient space, such as the attachment point of the tracking device 120 to the patient 14. A processor, such as the one included in the navigation system, or the user can identify points in the image data identical or related to the points identified with the tracking device 120. Thus, registration can occur.

It will be understood, however, that more than a single tracking device can be associated with the patient during imaging. Further, multiple tracking devices can be placed at multiple locations on the patient 14. If selected, the location of each of the multiple tracking devices can be determined with the navigation system 10. This can allow multiple portions of the patient 14 to be tracked during image acquisition.

The tracking device associated with the patient 14 also need not be the optical tracking device 120. The tracking device used during image acquisition can be any appropriate tracking device, such as an EM tracking device, including the EM tracking device 130 discussed herein. The imaging device 12, as discussed above, can also be tracked with an EM tracking device. Accordingly, the EM localizer 84 can be used to track an EM tracking device on the patient 14 and on the imaging device 12 during image acquisition.

In addition, the tracking device 120 can include fiducial points that can be imaged with the imaging device 12. Thus, the tracking device, which is tracked with the tracking system, is at a known position to the fiducial points. The fiducial points can also be identified in the image data. Again, this allows registration.

As illustrated in FIG. 4A, image data of one or more selected vertebra of the patient 14 can be imaged. The optical tracking device 120 can be interconnected with the base or connecting portion 122 of the vertebra that is imaged. Once the optical tracking device 120 is tracked or localized with the localizer 94, the image space can be substantially registered relative to the patient space by knowing the position of the imaging device 12, with the tracking device 37, and the position of the patient 14, with the optical tracking device 120. As is generally understood in the art, once the translation map is generated between the image data and the patient space any point in the patient space can be illustrated with the display device 74 and relative to the image data 77.

As discussed above, the navigation system 10 allows the physical position of a member, such as the instrument 90, to be illustrated relative to the image data due to registration of the image space and patient space. The image space being the space defined by the image data and the patient or subject space being the physical space defined by and relative to the patient. The navigation system includes one or more tracking systems to track the instrument 90 and/or other physical members in the patient space.

As discussed in greater detail herein, the tracking system can use alternative or multiple tracking systems. As illustrated in FIGS. 4A and 4B, the electromagnetic localizer 84 can also be used to track a tracking device, such as the electromagnetic (EM) tracking device 130 which can be used as a DRF. It will be understood that the EM localizer 84 can be provided in any appropriate size, such as about 15 cm across the front face and the illustrated dimensions are for clarity of the present disclosure. The EM tracking device 130 can be connected to the base 122 that remains connected to the patient 14. To enable the EM tracking device 130 to be connected to the base 122, the optical tracking device 120 can first be removed. Thus, both the EM tracking device 130 and the optical tracking device can be connected to the same base 122 for tracking the patient 14.

Figure 5:
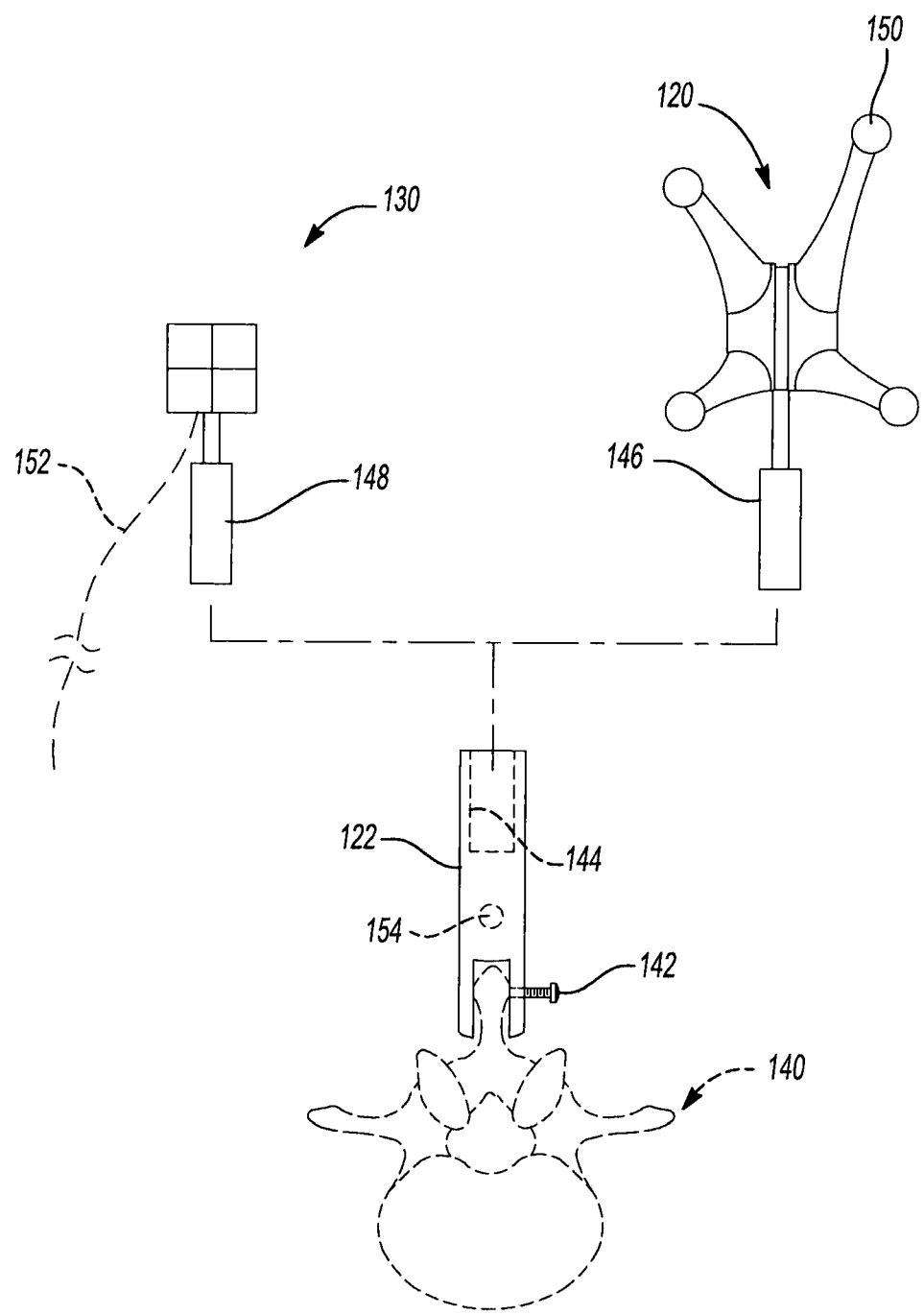

A selected point relative to the base 122 can be determined using both the optical tracking device 120 and the EM tracking device 130. For example, a central axis of the base 122 and a point 154 (FIG. 5) that is about 5 cm from the point of the connection of the base 122 with the patient 14 can be determined using both the optical tracking device 120 and EM tracking device 130. Using either of the optical tracking device 120 or the EM tracking device 130 to determine the single point 154 allows for an association or correlation between the navigation space defined by the optical localizer 94 and the navigation space defined by the EM localizer 84. Once the optical and the EM tracking systems are correlated, any appropriate tracking device can be used to track the instrument 90 relative to the patient 14, regardless of the type of tracking device associated with the instrument 90.

In further detail, correlation of the two tracking systems, such as the optical tracking system and the EM tracking system can be performed by identifying the single point 154 in the navigation spaces of both the EM tracking system and the optical tracking system. It will be understood, the navigation spaces of the EM and optical tracking systems can overlap or be completely separate, but the position of the single point 154 can be determined relative to the patient space and be determined in the image space to allow for correlation between the two tracking systems.

The determination of the single point 154 in both of the navigation spaces can be done by tracking or determining a location of both the optical tracking device 120 and the EM tracking device 130. Once the single point 154 is identified in both of the navigation spaces, the remaining points in both the navigation spaces can be correlated relative to the patient space within the image data. It will be further understood, the single reference point 154 can include multiple reference points and is one or more points within a navigation space that can be identified as identical to or at a known position relative to a point in another navigation space.

It will be further understood that any appropriate tracking system can be used, such as a radar or acoustic tracking system, and the illustration of the optical tracking localizer 94 and an EM tracking localizer 84 is simply exemplary. In addition, it will be understood, as further discussed herein, that both of the tracking systems can be used substantially simultaneously for tracking one or more portions, such as the patient 14 and the instrument 90. In addition, the localizers can be positioned in any appropriate location. For example, the EM localizer can be associated or connected to the housing 20. Additionally, as illustrated specifically in FIG. 4B, once at least one of the tracking systems is registered to the patient space, the imaging device 12 need not be present. Though the optical localizer 94 can be used to track the imaging device 12 during acquisition of the image data, once the image data is acquired with the imaging device 12, while being tracked with a selected tracking system, the imaging device 12 can be removed. The correlation with a second tracking system can occur by using a second tracking device, as discussed herein.

It will be further understood that the tracking systems can be used to track any appropriate instrument relative to any appropriate system, such as tracking an instrument relative to a mechanical system (e.g. aerospace systems, automobile systems, etc.) In addition more than one system, such as both of the optical and the EM tracking systems, can be used to track a single or multiple tracking devices substantially simultaneously. As understood by one skilled in the art, the tracking system, including the navigation processor 72, can be provided to determine and calculate the appropriate location of one or more tracking devices relative to the image data 77. Examples of appropriate navigation systems include STEALTHSTATION® AXIEM™, or TRIA® Plus, both sold by Medtronic Navigation, Inc.

As illustrated in FIGS. 4A and 4B, the single base or mount 122, or appropriate mounting portion, can be connected to the patient 14 to allow for interconnection of the selected optical tracking device 120 or the EM tracking device 130 with the patient 14. As specifically illustrated in FIG. 5, the mount 122 can be mounted to a portion or projection of a vertebra 140. The mount 122 can include a clamp or set screw 142 that can pass through or compress a portion of the mount 122 with the vertebra 140. The mount 122 can include a receiving portion or mounting portion 144 that engages an optical mounting portion 146 or an EM mounting portion 148. The receiving or mounting portion of the mount 122 can calibrated position/orientation specific configuration relative to the respective mounting portions of the optical and EM trackable portions 146, 148. Calibration can include determining an orientation of the optical and EM trackable portions 146, 148 or a keyed interconnection between the mounting portion of the mount 122 and the optical and EM trackable portions 146, 148. This can allow the tracking devices 120, 130 to be positioned relative to the mount 122 in a substantially repeatable and known position.

As is understood by one skilled in the art, the optical tracking device 120 can include one or more reflective or actively emitting optical portions 150 that can be sensed with the optical localizer 94. If the optical portions 150 are reflective, the optical localizer or any appropriate portion can emit an energy, such as infrared or visible light energy, to be reflected and sensed by the optical localizer 94. The EM tracking device 130 can include an electromagnetic coil that can sense or generate an electromagnetic field. The transmission of information regarding the sensed field can be sent wirelessly or via a wire 152 to the navigation processor 72 through the navigation probe interface 88.

Because each of the tracking devices 120, 130 can be interconnected with the mount 122 in a substantially known and precise manner, a position of the reference point 154 can be determined using either and/or both of the tracking systems and the tracking devices 120, 130. The tracking point or reference point 154 can be any appropriate point relative to the mount 122 and is illustrated as within the mount 122 simply as an example.

With reference to FIG. 6, the mount 122, or any appropriate mounting bracket, can be interconnected with a portion of the patient 14, such as the vertebra 140. The mount 122, as discussed above, can include a compression portion or a set screw 142. The mount 122 can include a mounting portion or a mounting receiving portion 144. The mounting portion 144 can connect to a post 160. The post 160 can incorporate or have mounted thereon an EM tracking device 162. If the EM tracking device 162 transmits a signal via a wire 164 it can also be interconnected with the post 160. The EM tracking device 162 can work similarly to the EM tracking device 130 in sensing or emitting a field.

The post 160, however, when interconnected with the mounting bracket 122, can further connect directly with an optical tracking device 170. The optical tracking device 170 can include an engageable region or area. The engageable region or area can include a passage or depression 172 to connect with the post 160. A set pin or spring loaded pin 174 can pass through a portion of the optical tracking device 170 to hold the optical tracking device 170 relative to the post 160. When the optical tracking device 170 is held relative to the EM tracking device 130 the two tracking devices, including the respective optical and EM tracking portions, can cooperate to allow tracking of a single portion with both tracking devices.

In this way, both of the EM tracking devices 162 and the optical tracking device 170 can be connected with the mount 122 substantially simultaneously. Again, a single reference point 154 can be determined with both of the EM tracking device 162 and the optical tracking device 170. The optical tracking device 170 can then be easily removed from the post 160 by use of the set pin 174 at a selected time. Nevertheless, when both of the EM tracking device 162 and the optical tracking device 170 are connected together and to the mount 122, the reference point 154 can be tracked or located in both of the respective tracking systems. Also, either of the respective tracking systems, optical or electromagnetic, can both determine the position of the reference point 154 and the optical tracking device 170 can be removed from the post 160 and the EM tracking device 162 can continue to be tracked or be used as a DRF.

With reference to FIG. 7, the mount 122 as discussed above, can be interconnected with a vertebra 140. A tracking device or assembly 180 can be interconnected with the mount 122 by connecting with a receiving or mounting portion 144. The tracking assembly 180 can include a tracking plate or member 182 onto which can be assembled or into which can be incorporated one or more EM tracking devices 184 and one or more optical tracking portions 186a-c.

As discussed above, the EM tracking device 184 can generate or sense an electromagnetic field. The EM tracking device 184 can transmit information via a wire 188 if selected. The optical tracking devices 186a-186c can emit appropriate optical energy or reflect optical energy to be tracked with a localizing device 94.

The tracking member 182 can be substantially rigid or formable in a substantially known and fixable manner. For example, the tracking member 182 can be provided in multiple pieces or fold along a folding or movable joint 190, but be fixed in a selected position relative to the mount 122. When fixed, the tracking member 182 can be used with the trackable portions to determine the location with the reference point 154 relative to the mount 122.

Because both of the EM tracking device 184 and the optical tracking portions 186a-186c are connected to the tracking member 182, both the EM and the optical tracking systems can be used to track or determine the reference point 154 substantially simultaneously. Because both of the optical tracking portions 186a-186c and the EM tracking device 184 are fixedly positioned relative to the member 182 and to each other, determining the reference point 154 or providing a dynamic reference frame individually within both of the EM and the optical tracking systems can occur. This allows for both the optical and the EM tracking systems to be correlated to one another due to the determination of a reference point with both the tracking systems. The reference point can be a single point determined with the EM tracking device 184 and the optical tracking portions 186a-c. Again, it will be understood, that the tracking assembly 180 can be both a DRF and used to track any appropriate instrument relative to the patient 14.

With reference to FIG. 8, a tracking assembly 180' can be provided that is substantially similar to the tracking assembly 180 illustrated in FIG. 7. The tracking assembly 180' can include one or more EM tracking devices 184' and one or more optical tracking portions 186a-c'. Again, the EM tracking device 184' can transmit information via a wire 188'.

The tracking assembly 180', however, can be interconnected with an instrument such as the instrument 90, discussed above, or an instrument or pointer probe 190. The probe 190 can be used with the tracking assembly 180' in both the EM and optical tracking systems to track any appropriate portion of the instrument 190, such as a tip 192.

Tracking the tip 192 of the instrument or probe 190 can allow for a determination of a point of the tip 192 within either of the tracking systems, including the optical or EM tracking system. This can allow for the determination of a reference point, such as the reference point 154, in both the EM and optical tracking systems. For example, to register the patient space and the image space, the user 81 can touch a point or multiple points in the patient space and also determine or identify the similar points in the image space to register the patient space to the image space.

Because the instrument 190 is tracked with both the EM and the optical tracking systems, the registration can be done in both of the tracking systems, including the EM and optical tracking systems, substantially simultaneously. Accordingly, the single act of determining points or determining fiducials in the patient space can be used to correlate the two tracking systems during the registration. Because both of the fiducial or registration points are identified with both of the tracking systems, both of the tracking systems can be registered to the image space and be correlated to one another due to the identification of the same fiducial points.

In addition, the tracking assemblies 180 or 180' can be used to identify or track an instrument substantially continuously during a procedure with either or both tracking systems. Because the tracking members 182, 182' include both the EM tracking devices 184, 184' and the optical tracking portions 186a-c, 186a-c', both of the tracking systems can be used to track the instrument to which the tracking members 182, 182' are connected.

It will be further understood that the optical tracking portions 186a-186c can be provided in any shape, number, or position as selected. Providing three, four, or any appropriate number of the optical tracking portions, according to various embodiments, is merely exemplary.

Figure 9:
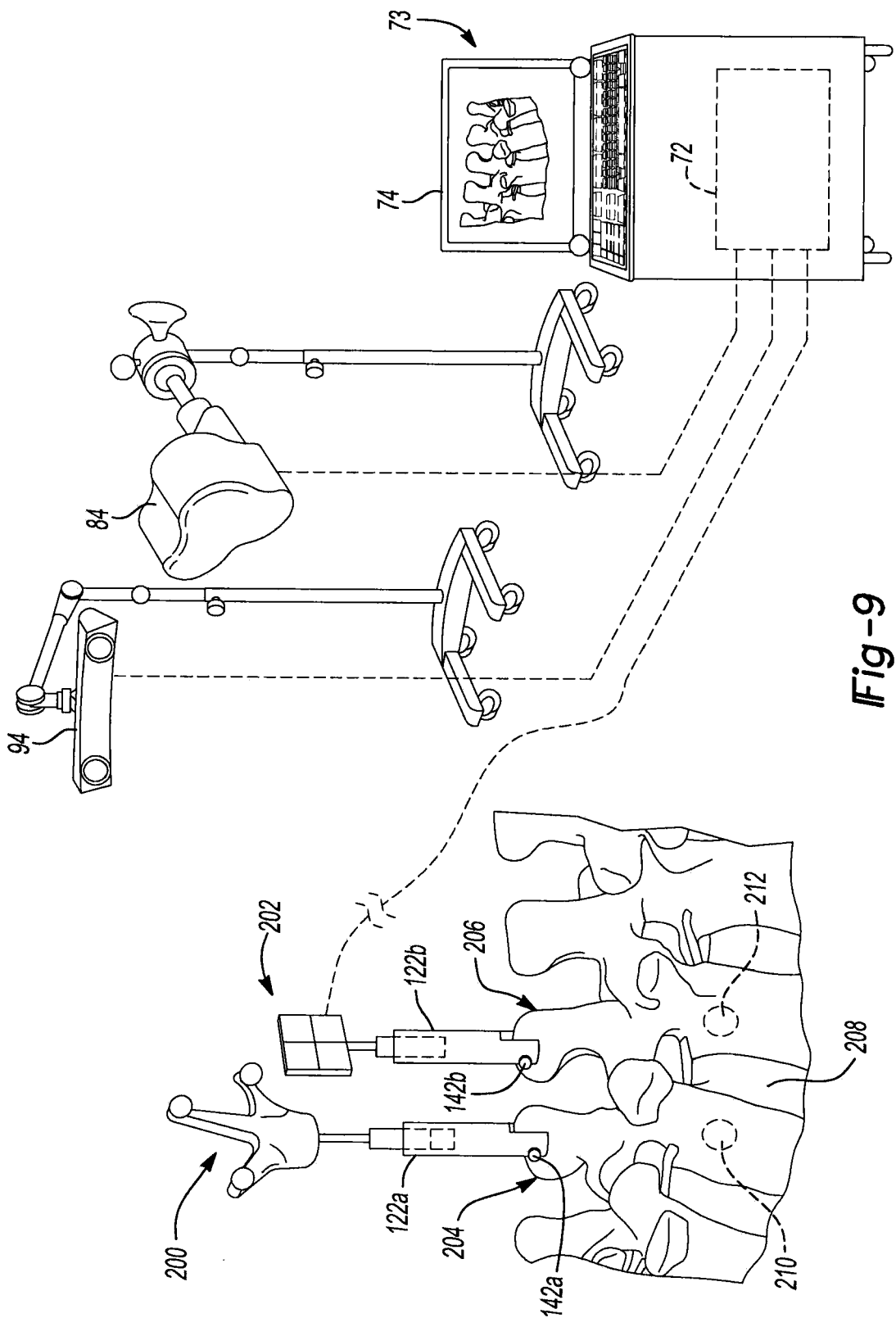

With reference to FIG. 9, according to various embodiments, an optical tracking device 200 can be positioned relative to an EM tracking device 202, and both can be used to correlate both an EM and an optical tracking systems. The optical localizer 94 and the electromagnetic localizer 84 can be used, substantially simultaneously or serially, to track or determine the position of the respective tracking devices 200, 202. The optical tracking device 200 can be connected to any appropriate portion of an anatomy, such as a first vertebra 204. The EM tracking device can be connected to any other appropriate portion of the anatomy, such as the same vertebra 204 or a second or different vertebra 206. Between the two vertebrae 204, 206 can be an intervertebral disc 208. Various tissues or portions, such as fusion implants, can also be used to hold the first vertebra 204 and the second vertebra 206 at a substantially fixed position relative to one another.

A reference point on the two vertebrae 204, 206 can be determined using both of the tracking devices 200, 202. It will be understood, however, that the reference point can be positioned at any point relative to the patient 14 and in the vertebrae 204, 206 is merely exemplary. For example, however, a first reference point 210 can be determined within the first vertebra 204 and a second reference point 212 can be determined within the second vertebra 206. As discussed above, the imaging device 12 can be used to acquire image data of the patient 14 and it can include image data of the first vertebra 204 and the second vertebra 206. In the image data, the position of the first vertebra 204 and the second vertebra 206 can be identified. The reference points 210, 212 can also be identified relative to the imaged vertebrae in the image data. Accordingly, determining the position of the reference points 210, 212 with the respective tracking devices 200, 202 can be used to correlate the two tracking systems because measurements can be made using the image data to precisely determine the position of the two reference points measured or determined with the two tracking devices.

With reference to FIG. 10, a method of correlating at least two tracking systems is illustrated in a flowchart 300. The method can start in start block 302. After starting the procedure, a tracking device can be attached to the imaging device in block 304. It will be understood, however, that the imaging device may inherently include or already have attached thereto a tracking device.

The imaging device 12 can be tracked in a first navigation space in block 306. As discussed above, the tracking device 37 can be attached to the imaging device 12 to track the position of the imaging device 12 in the first navigation space. A subject, such as the patient 14, can also be tracked in the first navigation space in block 308. For example, as illustrated above, the tracking device 120 can be attached to the patient 14 to track the patient 14 in the first navigation space, which can be defined with an optical tracking system. Therefore, both the imaging device 12 and the patient 14 can be tracked in the same navigation space defined by the first tracking system, which may include the optical localizer 94.

Image data can be acquired in block 310 while tracking both the imaging device in block 306 and the subject in block 308. The position of the image acquisition portion of the imaging device can be determined relative to the subject in block 312. As discussed above, the imaging device 12 can include the O-Arm® Imaging System sold by Medtronic, Inc., which can allow for a substantially precise determination of a position of the image acquisition portion. In addition, tracking the imaging device 12 in the first navigation space and tracking the subject in the first navigation space can allow for a determination of a position of the image acquisition portion relative to the subject, such as the patient 14.

In further explanation, determining a position of the image acquisition portion 22 relative to the gantry housing 20 of the imaging device 12 can be performed. The tracking device 37 can be attached to the gantry housing 20. Thus, the position of the gantry housing 20 is known in the navigation space and the position of the image acquisition portion 22 is known relative to the gantry housing 20. Thus, the image acquisition portion 22 can be known in the first navigation space.

Determining the position of the image acquisition portion can allow for a determination of the position of the image data in block 314. That determination can allow or determine a position of the image data relative to the subject. The position of the image data relative to the subject can be determined by fixing the subject relative to at least a portion of the imaging device or the image acquisition portion. Alternatively, or in addition thereto, determining the position of the image data can be based upon the determined position of the image acquisition portion relative to the subject in block 312.

Once the image data has been acquired while tracking the imaging device and the subject in blocks 306 and 308, a registration can be determined in block 316. As discussed above, the registration is between the image data defining the image space and the subject defining the subject space. The registration can be inherent or substantially automatic based upon the tracked position of the imaging device and the subject. As is understood by one skilled in the art, identifying multiple points or fiducial points in the image data or subject space, can be used to register the image space and the subject space. However, because the position of the image data is known relative to the position of the subject via tracking in the first navigation space identifying, physically or manually identifying discreet points is not necessary as the positions of the two are known for registration. The registration can be performed substantially automatically, such as with the navigation processor 72.

According to various embodiments, registration can be between the image data and one or a first tracking system. According, the subject is tracked in the first navigation space and the imaging device can be tracking in the first navigation space. Thus, the image data and the subject space can be registered with the first navigation space. As discussed herein, this registration can be used to correlate a second navigation space to the image space to allow a registration of the image data and the second tracking system or second navigation space.

With the registered image data and the subject space, navigation can occur relative to the image data using the first tracking device. If a second tracking system including a second navigation space is selected to be used, then a correlation between the two tracking systems can occur. The correlation can generally include the method portions identified in blocks 318-324. It will be understood that the first and second tracking systems can operate in substantially different manners or modalities, such as the first tracking system being an optical tracking system and the second tracking system being an electromagnetic tracking system.

The correlation can occur by identifying a reference point in both the first and the second navigation spaces. Determining a first reference point with a first tracking device in the first tracking system and in the first navigation space can occur in block 318. Determining a second reference point with a second tracking device and in a second navigation space can occur in block 320. Correlation of the first reference point and the second reference point can occur in block 322. The correlation can include determining that the first reference point and the second reference point are the same points in subject space or can include a plurality of identical points in subject space. Alternatively, as discussed above, the correlation of the first reference point and the second reference point can be two points that are not the same point in the subject space, but can be substantially precisely located relative to one another in the subject space, such as using the registered image data.

Once a correlation of one or more reference points has been made in block 322, the first navigation space and the second navigation space can be correlated in block 324. The correlation of the first and second navigation spaces can occur by determining a translation map between the first and second navigation spaces based upon the correlated first and second reference points or any appropriate number of reference points. As one skilled in the art will understand, registration between the image space and the subject space can be determined by registering or correlating identical points in the image space and the patient space. Thus, when the first and second navigation spaces have been correlated a translation map can be generated between the first ad second navigation spaces. Spatial calculations can be made based upon the reference points in the first and second navigation spaces to correlate all of the points in the first and second navigation spaces. Again, the first and second navigation spaces can be entirely separate, overlap partially, or overlap completely. Therefore, the first and second reference points can be at a single physical location in subject space but at different locations within the first and second navigation spaces.

Once the correlation between the first and second navigation spaces has occurred, a registration with the second tracking system and the second navigation space to the image data can occur in block 326. This can be determined because the first navigation space or the first tracking system has been registered to the image data. Once the correlation between the first and second navigation space has been made, that correlation can be used to determine a registration between the image data and the second tracking system. Accordingly, an instrument can be navigated using the second tracking system with the registered image data in block 328. A navigated procedure can then be performed in block 330, such as a spinal fusion, spinal implant, biopsy procedure, neurological procedure, orthopedic procedure, or any appropriate procedure. The method can then end in block 332.

According to the method outlined in flowchart 300, an imaging device can be used to acquire image data of a subject, such as a patient or any appropriate physical system or assembly, and more than one tracking system can be used to track an instrument relative to the subject. The two tracking systems can be registered to the image data after registering a single one of the tracking systems relative to the image data based upon correlating the first and second tracking systems. The correlation of the first and second tracking systems can occur by identifying reference points of the first and second navigation spaces to correlate the first and second navigation spaces of the first and second tracking system.

As discussed above, the imaging system 12 which can be provided as the O-arm® imaging system, sold by Medtronic, Inc. and can provide a selected image data of the patient 14. The image acquisition portion of the O-arm® imaging system can allow for a substantially precise positioning of the image acquisition portion relative to the patient 14. This can allow the position of the image acquisition portion to be precisely identified relative to the tracking device 37 without positioning the tracking device 37 on the image acquisition portion directly. Further, the second tracking system, such as the EM tracking system including the EM localizer 84, can be used after correlating the navigation space of the EM tracking system with a navigation space of the optical tracking system as discussed above.

The discussion herein of various processors or controllers, such as the navigation processor 72, can mean one or more individual physical processor cores, computers, etc. In addition, all of the various processor portions can be one or more computer programs executed by a single processor chip or core. The executed instructions and results can be saved in a memory system until called. Thus, the processors may include separated and distinct physical portions or may be executed by a single physical processor.

Using one or more tracking systems, whether or not different tracking modalities as used, can be provided for various purposes. For example, the optical localizer 94 operating in an optical modality may be unaffected by large metal objects, such as the imaging device 12. The EM localizer 84 may allow tracking of instruments without line of site to the instrument to be tracked. Accordingly, different tracking systems with different modalities can provide different advantages or properties. Also, two tracking systems, even if they are using the same modality, can be provided with different resolution, features, or spatial positions. Thus, allowing a correlation between two tracking systems, whether or not two different tracking modalities are used, can be selected.

As discussed above, the position of the tracking device that is associated with the patient 14 can be calibrated. As discussed herein, the optical tracking device 120 can be associated with the mount 122 and later the second EM tracking device 130 can be associated with the same mount 122. The two tracking devices can be calibrated relative to the location of the mount or their location relative to the patient 14.

Calibration can include a known specific orientation, such as with a keyed connection, of the respective tracking devices 120, 130 with the mount 122. For example, the mount 122, such as the receiving portion 144, can include a specific configuration, such as a flat or polygonal configuration, that mates in only a single configuration with the respective mounting portions 146, 148 of the tracking devices 120, 130. In this way, the tracking devices 120, 130 can interact or mate with the mount 122 in only a single configuration and orientation. Accordingly, the tracked portions of both of the tracking devices 120, 130 is known relative to the mount 122.

Alternatively, or in addition to a keyed or specific mounting configuration, the location or position of either or both of the tracking devices 120, 130 can be determined with a calibration measurement. In this manner, calibration of the location of the tracking devices can include inputting a specific location and orientation of the tracking devices 120, 130 into the navigation system 10. Alternatively, or in addition thereto, a tracked instrument, such as the tracked instruments 190, can be used to determine the position and/or orientation of the tracking device 120, 130 when connected or mounted in the mount 122. Accordingly, the navigation system 10 can determine the position of the tracking device 120, 130 without a requirement for predetermined position and/or orientation of the tracking device 120, 130 with the mount 122.

Calibration of the tracking device 120, 130 with the mount 122 can also include communication between the tracking device 120, 130 and the mount 122. For example, a position system can determine an orientation of the tracking device 120, 130 with the mount 122. The positioning system can include the mounting portion 144 having contacts on a surface of the mounting portion 144. The mounting portions 146, 148 of the tracking devices 120, 130 can include respective contacting portions to contact or complete a circuit between one or more of the contact portions within the mounting portion 144. By determining the contact portion connected, such as through the completion of the circuit, the orientation of the tracking device 120, 130 relative to the mount 122 can be determined. This can allow a position or orientation of the tracking device 120, 130 to be determined.

Accordingly, a position of the tracking device 120, 130 can be determined relative to the mounting device 122 in any appropriate manner. The position can be determined via a physical connection of the tracking device 120, 130 and the mount 122. The physical connection can include a keyed connection or position determining system. Alternatively, or in addition thereto, the position of the tracking device 120, 130 can be determined with a separate selected tracking instrument. Regardless of the method to calibrate or determine the location of the respective tracking devices 120, 130, or any appropriate tracking device relative to the mount or the patient 122, 14, respectively, the position of more than one tracking device relative to the mount 122 or the patient 14 can be determined.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A surgical navigation system, comprising:
   an imaging system operable to acquire image data, including:
      a rotor defining an imaging portion;
      a rail on which the rotor is operable to ride, wherein the rail surrounds at least a portion of a central opening;
      an emission portion and an image acquisition portion mounted to the rotor; and
      a gantry enclosing at least a portion of the rotor, the rail, the emission portion;
      an access to the central opening formed by the gantry including a first portion moveable relative to a second portion;
   a first tracking system operable in a first manner, wherein the first manner is an optical tracking configuration defining a first navigation space, including
      a first localizer having at least one camera operating in the first manner; and
      a first tracking device configured to be tracked using the first localizer having the at least one camera operating in the first manner;
   a second tracking system operable in a second manner that is electromagnetic and defining a second navigation space, including
      a second localizer having at least one coil operating in the second manner; and
      a second tracking device operable to be tracked using the second localizer having the at least one coil operating in the second manner;
   a third tracking device operable to be tracked by the first tracking system;
   a navigation system operable to execute instructions to determine a location of the first tracking device in the second navigation space, the second tracking device in the first navigation space, both the first tracking device and the second tracking device in the first navigation space, and both the first tracking device and the second tracking device in the second navigation space, due to correlation of the first navigation space and the second navigation space; and
   a single mounting structure operable to be connected to a patient at a selected location;
   wherein at least the third tracking device is positioned at a known position relative to the imaging system by being fixed to the gantry and the third tracking device is tracked to determine a position of the imaging portion of the imaging system within the first navigation space when the image data is acquired;
   wherein at least two of the first tracking device, the second tracking device, or the third tracking device are operable to be calibrated and selectively removably connected to the single mounting structure with a connection portion and operable to be connected to the single mounting structure separately while maintaining the single mounting structure connected to the patient.

2. The surgical navigation system of claim 1, wherein the emission portion and the imaging portion are positioned apart from each other when mounted to the rotor and within the gantry.

3. The surgical navigation system of claim 1, further comprising:
   an instrument operable to be fixedly connected to the single mounting structure;
   wherein a position of a selected portion of the instrument is operable to be tracked with either or both of the first tracking system and second tracking system when the single tracking member is connected to the instrument.

4. The surgical navigation system of claim 1, further comprising:
   wherein the second tracking device is operable to be connected directly to the single mounting structure;
   wherein the first tracking device is operably mounted to the second tracking device when the second tracking device is fixed to the single mounting structure;
   wherein a position of the first tracking device and the second tracking device are operable to be tracked when both are connected together and the second tracking device is connected to the single mounting structure using the respective first localizer or second localizer.

5. The surgical navigation system of claim 4, wherein the second tracking device includes a mounting portion extending a distance from the single mounting structure;
   wherein the first tracking device defines an engageable region operable to cooperate with the mounting portion;
   wherein the first tracking device further includes a locking member to lock the first tracking device relative to the second tracking device when the mounting portion is positioned at the engageable region.

6. The surgical navigation system of claim 1,
   the first tracking device and the second tracking device are mountable to the single mounting structure;
   wherein the single mounting structure is held relative to one another the first tracking device and the second tracking device;
   wherein using the first localizer and the second localizer the respective first tracking device and the second tracking device can be tracked when both are fixed to the single mounting structure.

7. The surgical navigation system of claim 6,
   wherein the single mounting structure is operable to be fixed to the patient at a selected location.

8. The surgical navigation system of claim 1, wherein the first tracking device is fixedly relative to a first position of the patient;
   wherein the second tracking device is operable to be fixed to a second position of the patient that is different than the first position of the patient;
   wherein the first position and the second position of the patient are known relative to one another in the first navigation space and the second navigation space.

9. The surgical navigation system of claim 8, wherein the first position is a first vertebrae of the patient and the second position is a second vertebrae of the patient that is different than the first vertebrae of the patient.

10. The surgical navigation system of claim 1, wherein the navigation system is operable to correlate the first navigation space of the first tracking system and the second navigation space of the second tracking system by the tracking of the first tracking device using the first localizer and tracking the second tracking device using the second localizer to determine the location of a reference point in both the first and second navigation spaces.

11. The surgical navigation system of claim 10,
wherein the reference point in both the first navigation space and second navigation space can be identified relative to the patient by positioning the first tracking device and second tracking device at a selected fixed location relative to the patient interchangeably via the single mounting structure.

12. A method of performing a navigated procedure, comprising;
tracking a gantry of an imaging system with a first tracking system using a first tracking modality;
wherein the imaging system comprises an emission portion on a rotor, wherein, the rotor is operable to move on a rail within the gantry, wherein the gantry has a central opening and an access to the central opening;
positioning an image acquisition portion at a known location relative to a subject with the gantry;
acquiring image data of the subject at the known location;
determining a position of the acquired image data relative to the subject based upon tracking the gantry of the imaging system and registering an image space in the acquired image data to a subject space of the subject based at least upon the determined position of the acquired image data;
determining a position of a first reference point relative to the subject by tracking the first tracking device with the first tracking system;
determining a position of a second reference point relative to the subject by tracking a second tracking device with a second tracking system using a second tracking modality different than the first tracking modality;
removably positioning the first tracking device and the second tracking device on a single mounting structure fixed to the subject, including positioning a portion of the first tracking device within a passage of the second tracking device and locking the second tracking device to the first tracking device;
correlating a first navigation space of the first tracking system and a second navigation space of the second tracking system using at least the determined position of the first reference point and the second reference point with both the first tracking system and the second tracking system based on the positioning the first tracking device and the second tracking device on the single mounting structure fixed to the subject to allow determination of a location of the first tracking device operated with the first modality in the second navigation space, the second tracking device operated in the second modality in the first navigation space, both the first tracking device and the second tracking device in the first navigation space, and both the first tracking device and the second tracking device in the second navigation space, due to correlation of the first navigation space and the second navigation space;
tracking a position of an instrument with only the second tracking system; and
illustrating the tracked position of the instrument relative to the image space using at least the correlated first navigation space and the second navigation space.

13. The method of claim 12, wherein determining the position of the first reference point relative to the subject by tracking the first tracking device with the first tracking system includes determining a first position of the first tracking device with an optical localizer having at least one camera; and
wherein determining the position of the second reference point relative to the subject by tracking the second tracking device with the second tracking system includes determining a second position of the second tracking device with an electromagnetic localizer by operating at least one coil.

14. The method of claim 12, further comprising:
fixing the first tracking device relative to the subject;
fixing the second tracking device to the first tracking device while the first tracking device is fixed relative to the subject;
tracking either or both of the first tracking device and the second tracking device while both the first tracking device and the second tracking device are affixed to the subject.

15. The method of claim 12, further comprising:
providing the single mounting structure having mounted thereon the first tracking device and the second tracking device at fixed positions; and
positioning the single mounting structure relative to the subject;
wherein tracking the first tracking device and tracking the second tracking device can occur simultaneously with the first tracking device and the second tracking device fixed relative to the single mounting structure.

16. The method of claim 12, further comprising:
providing an instrument connected with the single mounting structure;
wherein determining the position of the first reference point and the second reference point includes determining a position of a portion of the instrument by tracking both the first tracking device and the second tracking device fixed with relative to the single mounting structure.

17. The method of claim 16, further comprising:
moving the instrument to touch a fiducial point of the subject;
identifying the fiducial point in the image data to register the image data to the subject space; and
correlating the first navigation space and the second navigation space by determining the position on the instrument.

18. The method of claim 12, further comprising:
determining the first reference point and the second reference point relative to the first tracking device and the second tracking device mounted to the subject.

19. The method of claim 18, wherein the first tracking device is mounted at a distance from the second tracking device on the subject;
wherein the positions of each of the first reference point and the second reference point can be determined individually relative to either or both of the first tracking device and the second tracking device and the relative position of the first reference point and the second reference point can be further measured with the acquired image data; and
determining the position of the first reference point or the second reference point relative to the first tracking device or the second tracking device based upon the measurements with the acquired image data.

20. The method of claim 12, further comprising:
providing the image acquisition portion mounted on the rotor; and
providing the emission portion mounted on the rotor;

wherein positioning the image acquisition portion includes moving the rotor on the rail within the gantry wherein the image acquisition portion and the emission portion are positioned apart from one another with the subject between the emission portion and the image acquisition portion.

21. The method of claim 20, further comprising:
moving a portion of the gantry to allow lateral access to an interior central portion around which the gantry is formed, wherein the gantry is a housing and the portion of the gantry is a portion of the annular ring housing; and
moving the image acquisition portion within the housing.

22. The method of claim 21, wherein tracking the gantry includes positioning a third tracking device mounted on the gantry to be tracked with the first tracking system using the first tracking modality.

23. A surgical navigation system, comprising:
an imaging system operable to acquire image data including:
an annular gantry housing surrounding at least a portion of a central axis and forming a central opening,
a rail within the annular gantry,
a rotor operable to move on the rail,
an emission portion and an image acquisition portion mounted on the rotor
an access to the central opening, and
a mobile cart mounted to the annular gantry housing, wherein the annular gantry housing is operable to be positioned relative to the mobile cart in at least one of a vertical position, a horizontal position, and a rotational position;
a first tracking device connected with the imaging system;
a second tracking device and a third tracking device connected with a subject operable to be imaged with the imaging system;
a first tracking system operable in a first manner to track at least the first tracking device and the second tracking device in a first navigation space, including
a first localizer;
a second tracking system operable in a second manner different than the first manner to track the third tracking device in a second navigation space, including
a second localizer;
a navigation system operable to execute instructions to determine a location of the first tracking device and the second tracking device in the second navigation space and determine a location of the third tracking device in the second navigation space, and all of the first tracking device, the second tracking device, and the third tracking device in the first navigation space and the second navigation space; and
a single mounting structure operable to be connected to a patient at a selected location;
wherein at least both of the second tracking device and the third tracking device have a keyed connection portion operable to be removably connected to the single mounting structure separately while maintaining the single mounting structure connected to the patient;
wherein the navigation system is operable to correlate the first navigation space and the second navigation space due to tracking at least the second tracking device and the third tracking device.

24. The surgical navigation system of claim 23, wherein the first tracking system operating in the first manner is an optical tracking system and the first and the third tracking devices are operable to be tracked by only the first tracking system;
wherein the second tracking system operating in the second manner is an electromagnetic tracking system having at least one coil and the second tracking device is operable to be tracked only by the second tracking system.

25. The surgical navigation system of claim 23, wherein the second tracking device and the third tracking device are mounted on the single mounting structure;
wherein the single mounting structure is held relative to one another the second tracking device and the third tracking device;
wherein the first tracking system and the second tracking system are operable to track the respective second tracking device and the third tracking device when both are fixed to the single mounting structure.

26. The surgical navigation system of claim 23, further comprising:
an instrument operable to be fixedly connected to the single mounting structure;
wherein a position of a selected portion of the instrument is operable to be tracked with either or both of the first tracking system and second tracking system when the single mounting structure is connected to the instrument.

27. The surgical navigation system of claim 23, wherein the first tracking device is an optical tracking device operable to be localized with the first localizer which is an optical localizer having at least one camera;
wherein tracking the first tracking device with the optical localizer is unencumbered by the imaging system.

28. The surgical navigation system of claim 27, wherein the imaging system includes:
the rail surrounding at least a portion of the central axis;
the rotor operable to move on the rail around the central axis;
the emission portion and the imaging portion mounted on the rotor apart from one another and operable to move with the rotor around the central axis; and
wherein the annular gantry housing surrounds at least a portion of the rail, the rotor, the imaging portion, and the emission portion;
wherein the first tracking device is mounted on the annular gantry housing.

29. The surgical navigation system of claim 28, further comprising:
a moveable gantry housing portion;
wherein the moveable gantry housing portion is operable to move relative to the remaining annular gantry housing to provide a lateral passage to a central area of the annular gantry housing through the annular gantry housing and operable to allow a subject to pass through the passage to the central passage in the annular gantry housing.

30. The surgical navigation system of claim 29, wherein the subject is operable to be tracked relative to the annular gantry housing to allow for an inherent registration of image data acquired with the imaging system based at least in part on the first tracking device mounted on the annular gantry housing;
wherein the second tracking device and the third tracking device are operable to be positioned within an overlapping portion of the first navigation space and a second navigation space concurrent with or after the acquisition and registration of the image data with a subject space.

31. The surgical navigation system of claim 23,
wherein the third tracking device is operable to be connected directly to the single mounting structure;
wherein the second tracking device is operably mounted to the third tracking device when the third tracking device is fixed to the single mounting structure;
wherein a position of the second tracking device and the third tracking device is operable to be tracked when both are connected together and the second tracking device is connected to the single mounting structure with the respective first tracking system or second tracking system.

32. The surgical navigation system of claim 31, wherein the third tracking device includes a mounting portion extending a distance from the single mounting structure;
wherein the second tracking device defines a passage operable to cooperate with the mounting portion;
wherein the second tracking device further includes a locking member to lock the second tracking device relative to the third tracking device when the mounting portion is positioned within the depression.

33. The surgical navigation system of claim 23, wherein the second tracking device is fixedly connected to a first position of a patient;
wherein the third tracking device is operable to be fixed to a second position of the patient different than the first position of the patient;
wherein the first position and the second position of the patient are known relative to one another in a first navigation space and a second navigation space.

34. The surgical navigation system of claim 33, wherein the first position is a first vertebrae of the patient and the second position is a second vertebrae of the patient that is different than the first vertebrae of the patient.

35. The surgical navigation system of claim 23, wherein the navigation system is operable to correlate a first navigation space of the first tracking system and a second navigation space of the second navigation system by the tracking of the second tracking device with the first tracking system and tracking the third tracking device with the second tracking system to determine the location of a reference point in both the first and second navigation spaces.

36. The surgical navigation system of claim 35, wherein the reference point in both the first navigation space and second navigation space can be identified relative to a patient by positioning the second tracking device and third tracking device at a selected fixed location relative to the patient via a single mounting structure.

* * * * *